(12) United States Patent
Knudson et al.

(10) Patent No.: US 10,287,617 B2
(45) Date of Patent: May 14, 2019

(54) METHODS FOR IN VITRO—IN VIVO EFFICACY DETERMINATION

(71) Applicant: COLORADO STATE UNIVERSITY RESEARCH FOUNDATION, Fort Collins, CO (US)

(72) Inventors: Susan E. Knudson, Fort Collins, CO (US); Richard A. Slayden, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 200 days.

(21) Appl. No.: 15/124,651

(22) PCT Filed: Mar. 11, 2015

(86) PCT No.: PCT/US2015/019978
§ 371 (c)(1),
(2) Date: Sep. 8, 2016

(87) PCT Pub. No.: WO2015/138611
PCT Pub. Date: Sep. 17, 2015

(65) Prior Publication Data
US 2017/0081697 A1  Mar. 23, 2017
US 2018/0087085 A9  Mar. 29, 2018

Related U.S. Application Data

(60) Provisional application No. 61/951,412, filed on Mar. 11, 2014.

(51) Int. Cl.
*C12Q 1/18* (2006.01)

(52) U.S. Cl.
CPC ..................... *C12Q 1/18* (2013.01)

(58) Field of Classification Search
CPC ............ C12Q 1/18; G06K 13/06; G06K 7/00
See application file for complete search history.

(56) References Cited

U.S. PATENT DOCUMENTS

| | | |
|---|---|---|
| 8,039,502 B2 | 10/2011 | Chen et al. |
| 8,232,410 B2 | 7/2012 | Ojima et al. |
| 8,445,483 B1 | 5/2013 | Chen et al. |
| 8,741,944 B2 | 6/2014 | Chen et al. |
| 2006/0116412 A1 | 6/2006 | Ng et al. |
| 2009/0111799 A1 | 4/2009 | Chen et al. |
| 2010/0256203 A1 | 10/2010 | Ojima et al. |
| 2013/0109681 A1 | 5/2013 | Chen et al. |
| 2013/0237575 A1 | 9/2013 | Chen et al. |
| 2016/0297769 A1 | 10/2016 | Ojima et al. |

FOREIGN PATENT DOCUMENTS

| | | |
|---|---|---|
| WO | 2006130669 A1 | 10/2008 |
| WO | 2013116823 A1 | 8/2013 |
| WO | 2013142326 A1 | 9/2013 |

OTHER PUBLICATIONS

Pankey et al. Clin. Infectious Diseases (2004) 38: 864-870 (Year: 2004).*
Kumar et al. (J. Med. Chem. (2011) 54: 374-381 (Year: 2011).*
Zabranksy et al. Antimicrob. Agents Chemother. (1973) 3(2): 152-156 (Year: 1973).*
Awasthi, D., et al., "SAR Studies on Trisubstituted Benzimidazoles as Inhibitors of Mtb FtsZ for the Development of Novel Antitubercular Agents," J. Med. Chem.; 56(23):9756-9770; Nov. 23, 2013.
Franzblau, S.G., et al., Comprehensive Analysis of Methods Used for the Evaluation of Compounds Against *Mycobacterium tuberculosis*, Tuberculosis (Edinb).; 92(6):453-488; Nov. 2012.
Huang, Q., et al,, "FtsZ: A Novel Target for Tuberculosis Drug Discovery," Curr Top Med Chem.; 7(5):527-543; Feb. 2007.
Huang, Q., et al., "Targeting FtsZ for Antituberculosis Drug Discovery: Noncytotoxic Taxanes as Novel Antituberculosis Agents," J Med Chem.; 49(2):463-466; Jan. 26, 2006.
International Search Report of the ISA/US dated Oct. 5, 2015; Int'l Application No. PCT /US2015/019978 filed Mar. 11, 2015; Publication No. WO2015/138611A2 dated Sep. 17, 2015.
Knudson, S.E., et al., "A Trisubstituted Benzimidazole Cell Division Inhibitor with Efficacy against *Mycobacterium tuberculosis*," PLoS One; 9(4):e93953; Apr. 15, 2014.
Kumar, K, et al., "Novel Trisubstituted Benzimidazoles, Targeting Mtb FtsZ, As a New Class of Antitubercular Agents," J Med Chem.; 54(1):374-381; Jan. 13, 2011.
Kumar. K., et al., "Discovery of Anti-TB Agents that Target the Cell-division Protein FtsZ," Future Med Chem.; 2 (8):1305-1323; Aug. 2010.
Written Opinion of the ISA/US dated Oct. 5, 2015; Int'l Application No. PCT /US2015/019978 filed Mar. 11, 2015; Publication No. WO2015/138611A2 dated Sep. 17, 2015.

\* cited by examiner

*Primary Examiner* — Susan M Hanley
(74) *Attorney, Agent, or Firm* — Haukaas Fortius PLLC; Michael H. Haukaas

(57) ABSTRACT

The invention provides methods for determining and evaluating the in vitro-in vivo activity relationship of the efficacy of families of compounds for infectious diseases such as *tuberculosis*. The validity of the methods can be confirmed by evaluation of the compounds in animal models, for example, in murine models of *tuberculosis*. Examples of families of antibacterial compounds that can be evaluated for in vivo efficacy using the in vitro methods described herein include benzimidazoles, pyridopyrazines, pteridines, diphenyl ethers, beta-lactams, PBP inhibitors, and compounds that are non-ribonucleic acid and protein synthesis inhibitors. The methods can be used to evaluate classes of small molecule compounds and inhibitors that may be effective against any bacterial pathogen. The methods aid the identification of compounds, such as various benzimidazoles, with modes of action having activity against clinical isolates, as well as non-replicating persistent bacilli, which can therefore enhance current clinical therapeutic regimens.

16 Claims, 15 Drawing Sheets

METHODS FOR IN VITRO—IN VIVO EFFICACY DETERMINATION

RELATED APPLICATIONS

This application is a National Stage filing under 35 U.S.C. § 371 of International Application No. PCT/US2015/019978, filed Mar. 11, 2015, which claims priority under 35 U.S.C. § 119(e) to U.S. Provisional Patent Application No. 61/951,412 filed Mar. 11, 2014, which applications are incorporated herein by reference.

GOVERNMENT SUPPORT

This invention was made with government support under Grant Nos. AI078251 and AI082164 awarded by the National Institutes of Health. The government has certain rights in the invention.

BACKGROUND OF THE INVENTION

It is estimated that a third of the world's population is infected with *Mycobacteria tuberculosis*, the causative agent of *tuberculosis* (TB), and between 5-10% of those infected individuals will develop the active disease over their lifetime. As a result, TB is the second leading cause of death from an infectious disease and the leading cause of death from a bacterial infection worldwide. In addition to the global burden, the increasing rates of multi-drug resistant strains (MDR) that require extensive treatment regimens with second line drugs impacts disease management. Therefore, there is a need to develop new therapeutics with unique modes of action that can be used to treat TB or that can be co-administered with existing antitubercular drugs.

Cell division is an attractive target for the development of new chemotherapeutics against pathogenic bacteria, which are often medically important, difficult to treat, and drug resistant. One example is *Mycobacteria tuberculosis*. Of all the components involved in bacterial cell division two proteins, FtsZ and FtsI, are the best characterized and are therefore receiving the most attention with regards to drug discovery. Although, FtsZ and tubulin share structural and functional homology, specificity for the mycobacterial FtsZ can be obtained through medicinal chemistry efforts (Huang et al., *J. Med. Chem.* 2006; 49:463-466; Kumar et al., *J. Med. Chem.* 2011; 54:374-381). This specificity affords the opportunity to use known pharmacophores such as pyridopyrazine, pteridine and benzimidazole as starting points for SAR optimization. Certain 2,5,6- and 2,5,7-trisubstituted benzimidazoles developed through rational drug design have demonstrated potency with low or negligible cytotoxicity. However, the determination of their in vivo efficacy cannot be determined by analysis of their minimal inhibitory concentrations (MIC) alone, and adequate in vitro methods for determining in vivo efficacy are urgently needed.

SUMMARY

The invention provides methods for evaluating the in vitro-in vivo activity relationship of antibacterial compounds. The antibacterial compounds can be substituted benzimidazole cell division inhibitors with activity against *Mycobacteria tuberculosis*. In one embodiment, the invention provides a method for discerning a small molecular inhibitor having in vivo efficacy from a pool of antibacterial compounds by performing in vitro analyses and evaluating the analyses with respect to criteria developed to determine the in vivo efficacy of the inhibitor. In another embodiment, the invention provides a method for assessing the in vivo efficacy of a pool of antibacterial compounds by performing in vitro analyses. The methods can include:

(a) assessing the minimal inhibitory concentration (MIC) of a pool of antibacterial compounds with respect to an infectious bacteria;

(b) selecting one or more compounds from the pool of compounds, wherein the one or more selected compounds have lower MIC than the MIC of 50% of the pool of compounds;

(c) assessing the drug concentration response curve (kill-curve) of the selected compounds with respect to the infectious bacteria;

(d) identifying compounds from step (c) that display a multi-modal kill-curve, which kill-curve is characterized by a narrow range of concentrations of effective bactericidal activity, thereby indicating bacteriostatic activity above the MIC; and (d) identifying compounds from step (c) that display an inhibitory threshold as the concentration of the compound increases, thereby indicating bactericidal activity at the inhibitory threshold.

The combination of these steps, in any order, can be used to determine that the compounds identified in step (d) have less in vivo efficacy compared to the compounds identified in step (e). Accordingly, these methods allow for assessing the in vivo efficacy of one or more compounds in the pool of antibacterial compounds using only in vitro analyses. The compounds that lack in vivo efficacy based on the in vitro analyses can be eliminated from further consideration. The compounds that show in vivo efficacy based on the in vitro analyses can be selected for further study and/or can be submitted to structure-activity relationship studies. For example, the methods can further include selecting one or more compounds identified in step (e) for advancement into animal models of infection.

One or more compounds that display a multi-modal kill-curve may display a compound-tolerant phenotype by eliciting a stress response when assessing the drug concentration response curve of the compound.

The methods can further include an evaluation of the compounds for activity against clinical strains and non-replicating bacilli, and/or evaluation of cytotoxicity. For example, the pool of compounds can be evaluated for activity against clinical strains of an infectious bacteria, for activity against non-replicating bacilli, for cytotoxicity, for example, toward Vero cells, or a combination thereof.

The infectious bacteria can be, for example, *Mycobacteria tuberculosis, Francisella tularensis, Yersinia pestis*, or *Bacillus anthracis*. Specifically, the infectious bacteria can be a multidrug resistant (MDR) *M. tuberculosis*.

The one or more selected compounds having MIC lower than the MIC of 50% of the pool of compounds can be identified, forming a first subset of compounds, and the efficacy of the first subset of compounds can be assessed in an animal model of infection. The animal model can be, for example, a murine model of *tuberculosis*. One or more of the compounds in the pool of compounds can effectively kill *M. tuberculosis* cells or inhibit the growth of *M. tuberculosis* cells with an $MIC_{50}$ of less than about 15 μg/mL.

The pool of compounds can include 2,5,6-trisubstituted benzimidazoles, 2,5,7-trisubstituted benzimidazoles, or a combination thereof. In one embodiment, the 2,5,6-trisubstituted benzimidazoles comprise one or more compounds illustrated in FIG. 5-6, 11, or 14. SB-P1G10, SB-P3G2, or SB-P8B2:

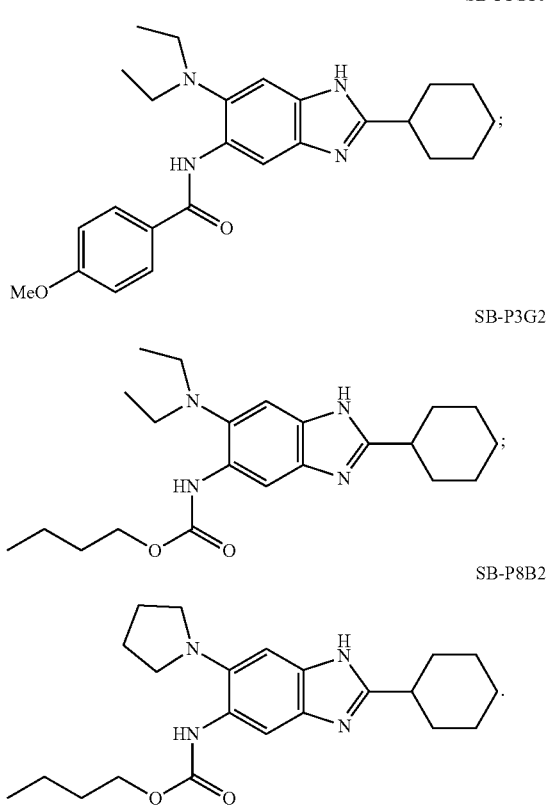

Other compounds that can included in the screen in various embodiments include the compounds illustrated or described in U.S. Pat. No. 8,232,410 and PCT Publication Nos. WO 2013/116823 and WO 2013/142326, which compounds are incorporated herein by reference.

The one or more selected compounds having MIC lower than the MIC of 50% of the pool of compounds can be identified, forming a first subset of compounds, and one or more compounds of the first subset can be evaluated in a long-term murine model of *tuberculosis*, can be evaluated in PK/PD studies, or a combination thereof.

The one or more selected compounds being characterized as being stable in human or mouse plasma, for example, with a less than 2% hydrolysis rate in human plasma and a less than 15% hydrolysis rate in mouse plasma, over a 4 hour time period.

The one or more selected compounds can be characterized as stable in the presence of human liver or mouse liver microsomes or microsomal proteins in that the metabolic conversion rate of the one or more selected compounds is less than 15% in the presence of human liver microsomes and less than 20% in the presence of mouse liver microsomes.

One or more of the selected compounds having MIC lower than the MIC of 50% of the pool of compounds can be identified as being not antagonistic with a second antibacterial drug. In some embodiments, one or more of the selected compounds having MIC lower than the MIC of 50% of the pool of compounds can be identified as being synergistic with a second antibacterial drug. The second drug can be, for example, isoniazid, bedaquiline, pyrazinamide, rifampin, ethambutol, or metronidazole.

Bacteria respond to in vivo drug exposure differently than to in vitro drug exposure. The invention provides methods to obtain new information (i.e., confirmation of in vivo efficacy) by discriminating between compounds that will be bactericidal in vivo and compounds that will be bactericidal/bacteriostatic in vivo. This information can be used to facilitate lead compound selection and the screening criteria for progression of drug candidates.

Thus, a major discovery described herein is the ability to categorize compounds as being either bactericidal or bactericidal, bacteriostatic (i.e., showing zonal inhibition), for which the bactericidal determination is an in vitro criteria for efficacy in models of infection, in contrast to the bactericidal/bacteriostatic determination, which typically do not show in vivo efficacy. Accordingly, the invention also provides a method of identifying a compound as having in vivo antibacterial efficacy from in vitro analysis comprising assessing an antibacterial compound as:

a) bactericidal above its minimal inhibitory concentration (MIC) in an in vitro assay and not bacteriostatic above its MIC, or b) bactericidal at its MIC in an in vitro assay and bacteriostatic above its MIC;

wherein a compound that is bactericidal above its MIC in an in vitro assay and not bacteriostatic above its MIC is therefore categorized as having in vivo antibacterial efficacy. The method can include one or more steps described above, as well as screening compounds using in vitro MIC analysis for in vivo antibacterial efficacy. The method can include carrying out the method described above on a plurality of compounds and performing animal studies on one or more compounds that are bactericidal above its minimal inhibitory concentration (MIC) in an in vitro assay and not bacteriostatic above its MIC. The compounds indicated as having in vivo efficacy can be combined with other compounds, such as isoniazid, bedaquiline, pyrazinamide, rifampin, ethambutol, or metronidazole, for the treatment of a bacterial infection.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

In drug development, it is often difficult to apply appropriate criteria to prioritize and advance drugs through the drug discovery pipeline. Most often, the advancement of lead compounds into animal models of infection to assess efficacy is based primarily on minimal inhibitory concentration (MIC) and cytotoxicity. Often, lack of efficacy is attributed to poor bioavailability or drug exposure. However, there is historical evidence that the bactericidal activity of some antimicrobials might not increase with additional drug. Rather, these compounds display a multi-modal kill-curve characterized by a narrow range of concentrations that result in effective bactericidal activity. A more recent study described that drug treatment can instigate a tolerant phenotype by eliciting alternate adaptive responses, which is consistent with this phenomenon, and the common observation of tolerance to treatment.

Previously, a library of 360 novel 2,5,6- and 2,5,7-trisubstituted benzimidazoles was synthesized as and screened against Mtb H37Rv (Kumar et al., *Future Med. Chem.* 2010; 2:1305-1323). From the assay, 27 compounds were identified that inhibited the Mtb cell growth with $MIC_{99}$ values at most 5 μg/mL in triplicates. Furthermore, among the 27 hits, nine compounds showed $MIC_{99}$ values at 0.56-6.1 μg/mL based on the more accurate Alamar blue assay. Upon further analysis, eleven 2,5,6- and 2,5,7-trisubstituted benzimidazoles were identified with significant potency against *M. tuberculosis* (Kumar et al., *J. Med. Chem.* 2011; 54:374-381). Although each of the lead compounds displayed attractive potency, it was unclear which of the trisubstituted benzimidazoles would be the best candidates for advancing into more resource-intensive long-term animal studies.

This disclosure provides methods for evaluating lead compounds that have similar physicochemical and in vitro potency against infectious microbes, such as *M. tuberculosis*, to determine which compounds are suitable drug candidates by eliminating compounds with ineffective in vitro inhibition kill-curve characteristics, to provide lead compounds with in vivo efficacy.

Figure 1:
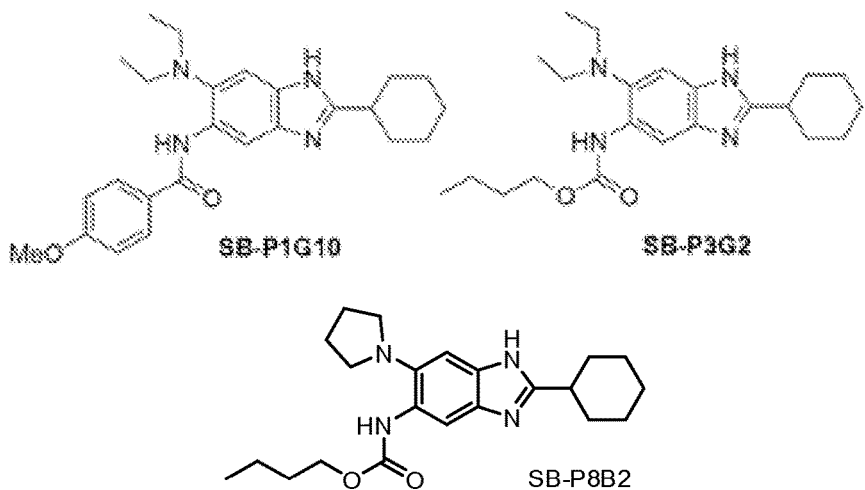
FIG. 1. Chemical structures for three 2,5,6-trisubstituted benzimidazoles.

Described herein is the analysis of various antibacterial compounds, including three lead 2,5,6-trisubstituted benzimidazoles, SB-P1G10, SB-P3G2 and SB-P8B2 (FIG. 1). These three lead compounds were evaluated in more detail for activity against clinical strains and non-replicating bacilli. The kill-curve characteristics of the lead compounds were determined and efficacy was assessed in murine models of *tuberculosis*. These studies revealed an in vitro-in vivo activity relationship of the anti-TB benzimidazoles exhibiting efficacy in a murine model of *tuberculosis*. Importantly, the identification of an in vitro-in vivo activity relationship was identified that can serve as a criterion for advancing next generation cell division inhibitors into more resource intensive efficacy models such as the long-term murine model of *tuberculosis* and Pre-IND PK/PD studies.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a test mixture, in vitro, or in vivo.

An "effective amount" refers to an amount effective to kill a cell, inhibit a cell from growing or dividing, treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition: and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

As used herein, minimal inhibitory concentration (MIC) refers to the concentration that completely inhibits visible growth of an organism as detected by the unaided eye after a 12 to 120 hour incubation period with a standard inoculum of approximately 105 CFU/mL. See Clinical Laboratory Standards Institutes, Methods for Dilution Antimicrobial Susceptibility Tests for Bacteria That Grow Aerobically; Approved Standard—Eighth Edition January 2009M07-A8, Vol. 29 No. 2, Replaces M07-A7, Vol. 26 No. 2; and Performance Standards for Antimicrobial Susceptibility Testing; Twentieth Informational Supplement January 2010, M100-S20, Vol. 30 No. 1, Replaces M100-S19, Vol. 29 No. 3.

The term $MIC_{99}$ refers to the minimum concentration of compound required to give a calculated 99% inhibition of bacterial growth.

Figure 5:
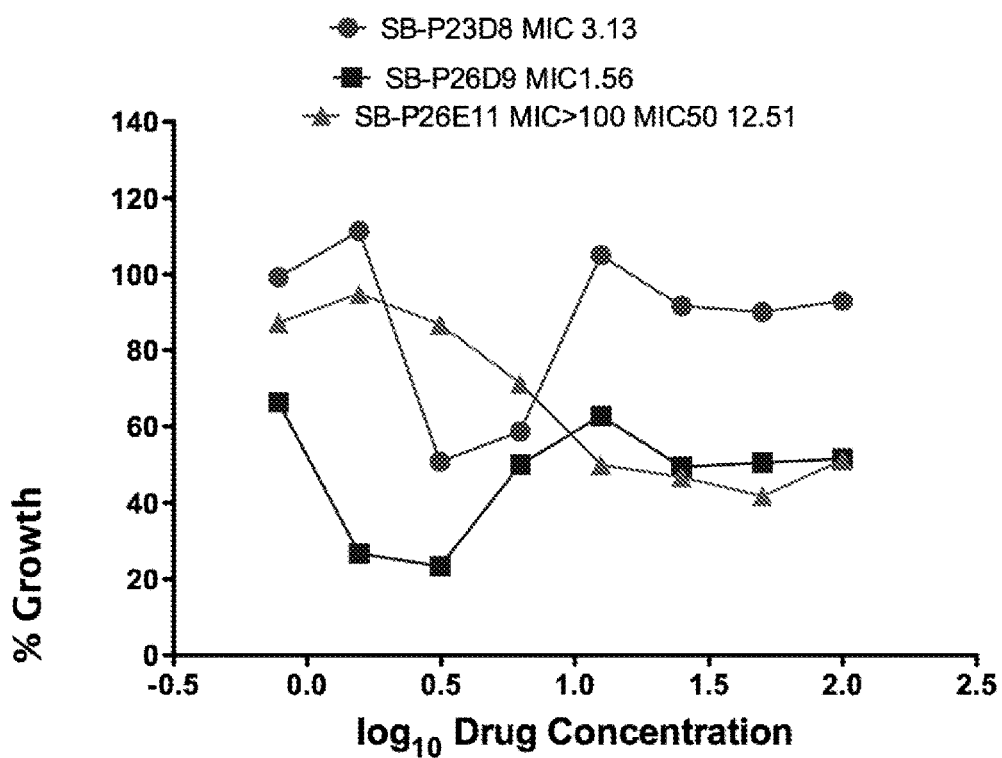
FIG. 5. Additional benzimidazole drug concentration response curves and relevant structures.
Figure 5:
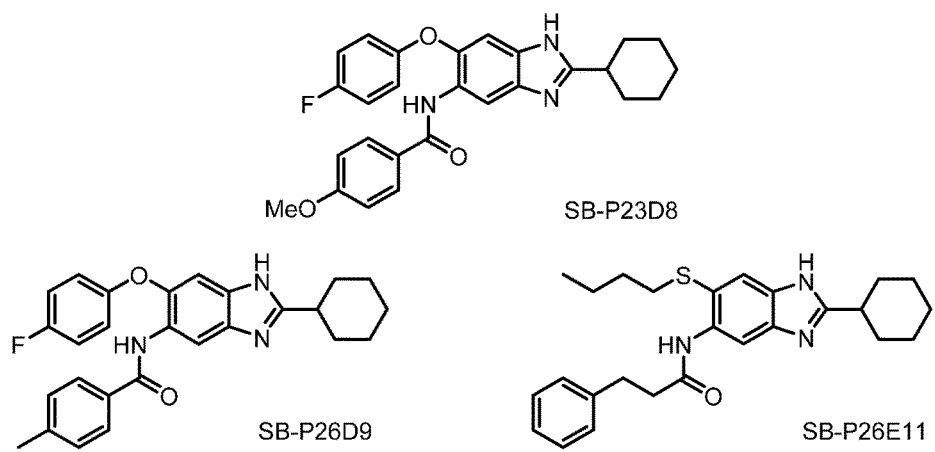

A narrow range of concentrations of effective bactericidal activity (NREBA) kill curve refers to a drug concentration response curve where the kill curve is non-sigmoidal and which displays a local minima with lesser growth inhibition values on either side. A drug concentration response curve can be generated by graphing the $log_{10}$ drug concentrations (µg/mL) against the difference in growth between the drug-treated wells and control wells. See FIG. 3C, and FIG. 5 (entries for SB-P23D8 and SB-P26D9). A NREBA is indicative of bacteriostatic activity above the MIC.

The term "inhibitory threshold" refers to a concentration at and above which a compound displays bactericidal activity.

The term "in vivo efficacy" refers to a statistically significant reduction in bacterial burden in infected tissues of interest (e.g., lungs, spleen, or liver), and/or a statistically significant increase in mean to morbidity and mortality (i.e., death).

The terms "stress response" or "adaptive response" refer to the response of a bacterium to environmental factors including the presence of an inhibitor that is not completely cytotoxic or biocidal at the levels present, which allows the bacterium to adapt and proliferate, which response can result in a non-sigmoidal drug response curve. See Miller et al., Science 2004; 305:1629-1631 for information on bacterial stress responses.

The phrase "pool of antibacterial compounds" refers to a group of compounds that include two or more compounds that possess antibacterial properties. A pool is often about 90 to about 100 compound. Larger pools can be evaluated by concurrent or sequential analysis of smaller pools.

In Vitro-In Vivo Activity Relationship of Substituted Benzimidazole Cell Division Inhibitors with Activity Against *Mycobacteria tuberculosis*.

The goal to reduce the global burden of *tuberculosis* has been hampered by difficult to treat chronic infections and the emergence of multiple drug resistant (MDR) strains of *M. tuberculosis* that are resistant to the frontline drugs or drug combinations needed to achieve durable cure. While drug discovery programs continue to make progress, there often remains a disconnect between a drug candidate's in vitro potency and its observed efficacy in models of infection, which limits the number of lead candidates advancing to Pre-IND and clinical evaluation. This disconnect, in part, can be attributed to differences in a compound's kill characteristics. The susceptibility of bacteria to a drug is primarily influenced by the concentration of the drug required to kill the bacteria and the rate at which the bacteria are killed at the appropriate concentration. This translates to efficacy because a drug that has a limited and pronounced zonal susceptibility and a slow killing rate will not demonstrate efficacy and therapeutic significance.

As part of our ongoing drug discovery program targeting FtsZ, three lead compounds were selected for more advanced in vitro characterization and efficacy testing. The in vitro-in vivo activity relationship of each of these compounds provides information about the drug exposure potential upon dosing in animal models of infection. MIC is the most common parameter used to prioritize a drug candidate's progression into efficacy studies. However, MIC as a primary criterion has limitations because it docs not provide information about the rate of killing (a slow rate allows for adaptive/stress responses) or the effective concentration (sigmoidal curve vs. narrow zone of inhibition) of drug to achieve the rate of killing. Although the MIC of different drug candidates may be similar, their kill-curve characteristics could be different, resulting in observed differences in efficacy when delivered in vivo. The invention provides methods to determine in vivo efficacy by evaluating certain in vitro parameters described herein, thereby reducing the number of compounds that require in vivo testing (even if they have sufficiently low MICs) and allowing for the selection of compounds that will have in vivo efficacy.

The kill-curves generated for both SB-P3G2 and SB-P8B2 were concentration dependent and sigmoidal (FIG. 3). This indicates that as the concentration of the compound increases, an inhibitory threshold is met and significant bactericidal activity is achieved. Importantly, the bactericidal activity is sustained despite significantly increased drug concentrations. This is consistent with the observed efficacy of SB-P3G2 in two different acute *tuberculosis* models of infection. These characteristics are typical of our lead compounds with efficacy in acute models of infection because at drug concentrations near the MIC, the growth rate and number of viable bacteria is reduced, and the maximal effective dose range is large. This allows effective therapeutic concentrations to be maintained at the site of infection throughout the dosing interval.

In contrast, the inhibition and dose response curves generated for SB-P1G10 showed a pronounced zonal susceptibility similar to what has been described as the Eagle-Musselman phenomenon (Eagle and Musselman, *J. Exp. Med.* 1948; 88:99-131). This type of kill-curve indicates that SB-P1G10 is bactericidal within a narrow range of concentrations centered on the MIC, but any increase in compound concentration greater than the optimal levels significantly reduces the extent of bacterial death. Therefore, the effective therapeutic concentration for SB-P1G10 within the narrow zone of susceptibility/bactericidality is maintained for only a very short time during dosing and typical dosing regimen push the active agent concentration to over, and therefore outside, the narrow zone of susceptibility/bactericidality, essentially eliminating efficacy and often causing drug resistance in the bacteria.

Together, the efficacy studies with SB-P3G2 and SB-P1G10 revealed the in vitro activity-efficacy relationship for these drug leads, and provide an explanation for the often observed disconnect between drug potency and treatment efficacy. This is further justified by a report that observed that bacterial tolerance is a result of drug exposure that has been shown to be the result of induction of stress responses (Miller et al., *Science* 2004; 305:1629-1631). This observation is consistent with the notion that compounds with a narrow zone of susceptibility lack significant in vivo efficacy because of the limited achievable and sustainable effective (narrow range) therapeutic concentrations.

A new drug for *tuberculosis* should be co-administrable with currently used clinical drugs, and should have activity against clinical strains with differing drug susceptibilities and potency against non-replicating persistent bacilli. We assessed whether the inhibition of cell division with SB-P8B2 was antagonistic when used in combination with rifampicin. The FICI for the rifampicin and SB-P8B2 combination was 0.63, indicating that these two drugs are not antagonistic. In addition, the activity of SB-P8B2 against *M. tuberculosis* was enhanced by 8-fold in the presence of rifampicin. Only a modest 2-fold increase in the activity of rifampicin was observed. It is thought that because bacterial adaption to stress, including the bacterial response to drug exposure, occurs at the level of protein synthesis, the observed enhancement of SB-P8B2 activity is the result of rifampicin preventing the bacterial response to treatment with SB-P8B2.

These lead drug candidates were shown to be equally active against clinical isolates and the laboratory strain, which is expected because the molecular target of this class of inhibitors is not a molecular target for current clinically used compounds. It is well known that the frontline TB drug isoniazid is only active against replicating *M. tuberculosis* typical of acute infections, and does not effectively kill non-replicating persistent organisms. Therefore, to assess whether cell division inhibitors have activity against non-replicating persistent bacilli, SB-P3G2 and SB-P8B2 were tested and both were found to be effective against non-replicating bacteria. SB-P1G10 was not tested under these conditions because at higher concentrations the compound is bacteriostatic.

A new anti-TB drug needs to be active against clinical strains with various drug susceptibility profiles as well as non-replicating persistent organisms. In addition, it should be co-administrable to improve treatment of chronic TB infections. Disclosed herein are methods to evaluate the in vitro-in vivo activity relationship of a lead benzimidazole's efficacy in murine models of *tuberculosis*. This disclosure also shows that selected benzimidazoles with this mode of action have activity against clinical isolates, as well as non-replicating persistent bacilli, and can enhance current therapeutic regimens. Together, these results substantiate that the molecular target FtsZ and this class of compounds is a clinically relevant target and a novel class of chemotherapeutic agents for the treatment of *tuberculosis*.

Figure 11:
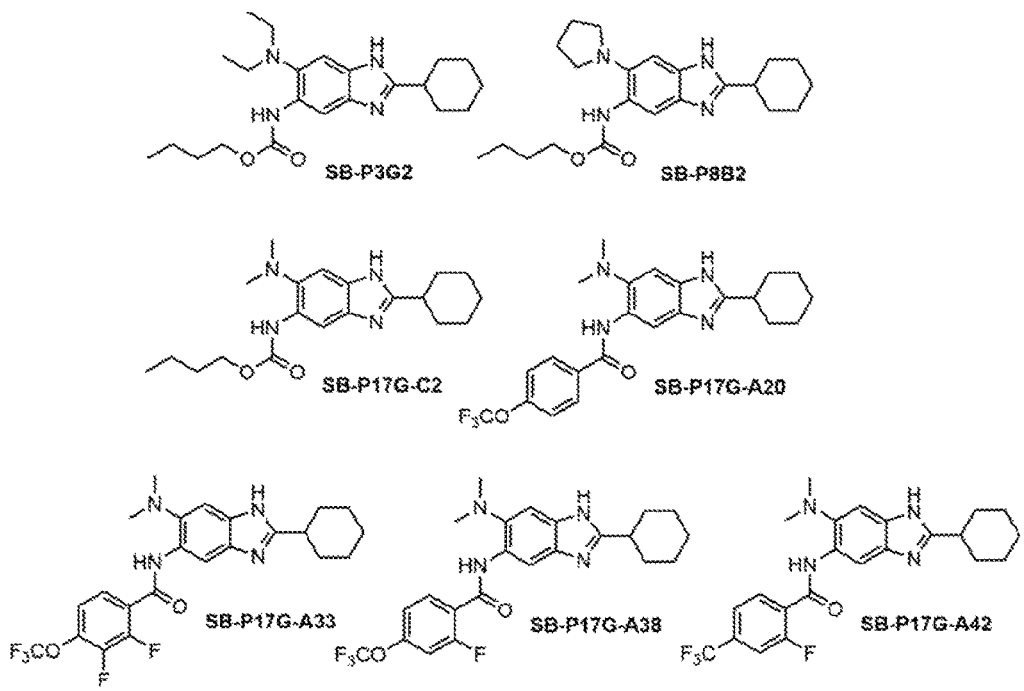
FIG. 11. Chemical structures of certain 2,5,6-trisubstituted benzimidazoles.

Further analysis using the methods described herein was performed on the compounds found in Tables A and B (bold font compounds are shown in FIG. 11) resulting in the data found therein.

TABLE A

Benzimidazoles activity tested in animals.

| Compound | MIC | Curve | Efficacy Lung | Efficacy Spleen |
|---|---|---|---|---|
| SBP3G2 | 1.25 | Sigmoid | Yes | Yes |
| SBP5C1 | 1.56 | Sigmoid | ND | ND |
| SBP8B4 | 3.13 | Sigmoid | None | None |
| SBP8B2 | .625 | Sigmoid | Yes (.243) | No |
| SB-P17G-A20 | .31 | Sigmoid | Yes | Yes |
| SB-P17G-C2 | .063 | Sigmoid | Yes (.3464) | No |
| SB-P17G-A16 | .31 | Sigmoid | Yes | Yes |
| SB-P17G-A33 | .5-.625 | Sigmoid | Yes | Yes |
| SB-P17G-A38 | .156 | Sigmoid | Yes | Yes |
| SB-P17G-A42 | .156 | Sigmoid | Yes | Yes |
| SB-P1G10 | 3.13-6.25 | Zonal | No | No |

ND: sufficient data not obtained

TABLE B

MIC and Drug Response Curve Type.

| Compound | MIC | Curve |
|---|---|---|
| SB-P6B-A3 | 12.5 | Zonal |
| SB-P1G-A4 | 12.5 | Zonal |
| SB-P1G-A11 | 12.5 | Zonal |
| SB-P1G-A12 | 12.5 | Zonal |
| SB-P1G-A21 | 25 | Zonal |
| SB-P2G-E11 | 12.5 | Zonal |
| SB-P1G10-FUM | 6.25 | Zonal |
| SB-P1G-A17 | 1.56 | Zonal |
| SB-P1G4 | 12.5 | Zonal |
| SB-P2G3 | 12.5 | Zonal |
| SB-P3B2 | 50 | Zonal |
| SB-P22C3 | 25 | Zonal |
| SB-P22C4 | 25 | Zonal |
| SB-P22C5 | 50 | Zonal |
| SB-P22C6 | 50 | Zonal |
| SB-P22C7 | 25 | Zonal |
| SB-P22C8 | 25 | Zonal |
| SB-P26D9 (5c) | 1.56 | Zonal |
| SB-P26F9 (5f) | 6.25 | Zonal |
| SB-P23D8 (5b) | 3.13 | Zonal |
| SB-P26H8 (5g) | 25 | Zonal |
| SB-P26F8 | 25 | Zonal |
| SB-oli-C8 | 6.25 | Zonal |
| SB-P27C7 | 6.25 | Zonal |
| SB-o13-(A)C23 | 1.25 | Zonal |
| SB-P1G8 | 3.13 | Zonal |
| SB-P27A9 | 12.5 | Zonal |
| SB-P17G-C4 | 12.5 | Zonal |

Interestingly, some compounds, for example SB-P17G-A33, SB-P17G-A38 and SB-P17G-A42, which are derivatives of compound SB-P17G-A20, showed favorable drug profiles to serve as next generation lead compounds. SB-P17G-A20 has a 4-trifluoromethoxy-benzoylamino group at the C5 position. However, the introduction of a fluorine into the ortho position of the 4-trifluoromethoxy-benzoyl or 4-trifluoromethylbenzoyl moiety substantially increased plasma and metabolic stability (see Table 3.2).

Moreover, compounds SB-P17G-A33, SB-P17G-A38 and SB-P17G-A42 showed extremely low MIC levels and were found to be non-toxic to Vero cells at a concentration of 200 μg/mL (see Table 3.1). These compounds were also able to reduce the bacterial load in an in vivo *tuberculosis* murine model of infection, as well as an in vitro testing to levels comparable to the frontline antitubercular drug, isoniazid (see FIG. 13 and Table 3.3).

The following Example is intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Methods for Improved In Vitro-In Vivo Efficacy Determination

Structure based drug design was used to develop a library of novel 2,5,6- and 2,5,7-trisubstituted benzimidazoles. Three lead compounds, SB-P1G10, SB-P8B2 and SB-P3G2, were selected from this library for advanced study into their in vitro characteristics, potency against clinical strains and non-replicating persistent bacilli, and their efficacy in murine models of *tuberculosis*. In vitro studies revealed that SB-P8B2 and SB-P3G2 had sigmoidal kill-curves while in contrast SB-P1G10 showed a narrow zonal susceptibility. The in vitro studies demonstrated that exposure to SB-P8B2 or SB-P3G2 was bactericidal, while SB-P1G10 treatment never resulted in complete killing (i.e., SB-P1G10 is bacteriostatic at elevated concentrations). The dose curves for the three compounds against clinical isolates were comparable to their respective dose curves in the laboratory strain of *M. tuberculosis*. SB-P8B2 and SB-P3G2 also exhibited antibacterial activity against non-replicating bacilli under low oxygen conditions.

SB-P3G2 and SB-P1G10 were assessed in acute short-term animal models of *tuberculosis*, which showed that SB-P3G2 treatment demonstrated activity against *M. tuberculosis*, revealing an in vitro-in vivo relationship of the 2,5,6-trisubstituted benzimidazoles that can serve as a criterion for advancing this class of cell division inhibitors into more resource intensive in vivo efficacy models such as the long-term murine model of *tuberculosis* and Pre-IND PK/PD studies. Specifically, these studies are the first demonstration of efficacy and an in vitro-in vivo activity relationship for antibacterial compounds such as 2,5,6-trisubstituted benzimidazoles. The in vivo activity presented herein substantiates this class of cell division inhibitors as having potency and efficacy against *M. tuberculosis*.

Methods.

*Mycobacteria tuberculosis* Strains and Drug Treatment Conditions.

*Mycobacterium tuberculosis* H37Rv and Erdman (TMCC 107) strains are drug sensitive laboratory reference strains used in the MIC studies, and used in the *tuberculosis* animal models of infection. The clinical isolates W210, NHN20, NHN382 and TN587 have varying drug susceptibility profiles. For the in vitro studies described herein, all strains were grown in Difco™ 7H9 Middlebrook liquid media (BD Biosciences, 271310) supplemented with 10% Middlebrook OADC Enrichment (VWR, 9000-614), 0.05% Tween (G-Biosciences, 786-519), and 0.2% glycerol at 37° C. *M. tuberculosis* was grown on Difco™ Middlebrook 7H11 agar (BD Biosciences, 283810) supplemented with 1% asparagine and antibiotics for colony forming unit (CFU) assays from animal studies. Antibiotics used were carbenicillin 50 mg/L (Sigma, C1389) and cycloheximide 10 mg/L (Sigma. C7698). Antibiotics and asparagine were not included in agar plates used for CFUs from *M. tuberculosis* in vitro assays. Three 2,5,6-trisubstituted benzimidazoles, SB-P1G10, SB-P3G2 and SB-P8B2, were synthesized as described previously (Kumar et al., *J. Med. Chem.* 2011; 54:374-381).

In Vitro Growth and Bactericidal Assays.

MIC values were determined for the benzimidazoles using a modified 96-well microplate Alamar Blue (resazurin) assay (MABA) (see Kumar et al., *J. Med. Chem.* 2011; 54:374-381; Collins and Franzblau, *Antimicrob. Agents Chemother.* 1997; 41:1004-1009). Dose response curves were generated from the MABA assay for compounds by graphing the $\log_{10}$ drug concentrations against the difference in growth between the drug-treated wells and control wells using GraphPad Prism Version 5.0d for Mac OS X (GraphPad Software, San Diego Calif., USA, www.graphpad.com). For time dose studies, bacterial growth in the presence of compound was monitored by the O.D. 600 nm. Each compound was assessed at a number of concentrations relative to the MIC in triplicate every 24 hours over 5 days by O.D. 600 nm and confirmed by plating at days 0, 1, 3, and 5 of drug exposure. The values were plotted against time using GraphPad Prism Version 5.0d for Mac OS X (GraphPad Software, San Diego Calif., USA, www.graphpad.com).

In Vitro Low Oxygen Studies.

The low oxygen studies were performed similar to those described previously (Lenaerts et al., *Antimicrob. Agents Chemother.* 2005; 49:2294-2301). Briefly, *M. tuberculosis* H37Rv were diluted to an O.D. 600 nm of 0.003 in 7H9 media containing Methylene Blue (1.5 μg/mL) and were grown in 16×125 mm Hungate tubes with rubber septa (VWR cat#89167-170). The tubes, with 11 mL of the diluted cultures were incubated at 37° C. under agitation (150 rpm). Methylene blue was monitored for color change indicating that oxygen was depleted from the system. One week after the reduction of methylene blue, approximately 28 days from the start, drug treatment was initiated with the test and control drugs. Prior to treatment, an aliquot was removed and plated for a CFU count to serve as a control. Isoniazid and metronidazole were used in the studies as comparative controls.

Recovery of aliquots for plating and the addition of drugs were conducted through septa using syringes to maintain the low-oxygen conditions. Ninety-six hours post-treatment, 1 mL of the culture was removed from the oxygen depleted cultures, the aliquot was serial diluted and the dilutions were plated. $\text{Log}_{10}$ CFUs were calculated for the different treatments and concentrations. Percentage growth reduction from the controls was calculated and reported.

In Vitro Drug Combination Studies.

A checkerboard 96 well plate method was used to examine possible antagonism or synergy between the lead 2,5,6-trisubstituted benzimidazoles and rifampicin (RIF). Drugs were distributed in 2-fold dilutions in a checkerboard pattern in a 96 well plate starting with 2×MIC for each drug tested in combination. *M. tuberculosis* H37Rv cells were added to the plate to a final well volume of 200 μL. No-growth and positive-growth controls were included in the assay. After 6 days of incubation at 37° C., Alamar Blue was added. Fractional inhibitory concentrations (FIC) were calculated to determine synergy in the drug combinations as described by Reddy et al. (*Antimicrob. Agents Chemother.* 2010; 54:2840-2846). FIC is defined as the MIC of a drug in combination divided by the MIC of that drug alone. The fractional inhibitory index (FICI) is the sum of the FICs (ΣFIC) for the drugs tested in the combination. Drugs are considered synergistic when the ΣFIC is less than 0.5, indifferent when the ΣFIC is between 0.5 and 4, and antagonistic when the ΣFIC is greater than 4.

Rapid Murine Models of *Tuberculosis* Used for Efficacy Screening.

Compound efficacy was assessed in two murine models of infection based on the short term model described previously (Lenaerts et al., Antimicrob. *Agents Chemother.* 2003; 47:783-785). All aerosol infections were performed using a Middlebrook aerosol generation devise (Glas-Col, Terre Haute, Ind.).

In the first infection model, immune incompetent C57BL/6-Ifngtm1 ts gamma interferon gene disruption (GKO) mice were infected with *M. tuberculosis* H37Rv. Animals were dosed q.d. IP beginning at day 12 post-infection with 150 mg/kg of compound in 38% ethanol and 10% Solutol (e.g., Solutol HS 15) for 9 consecutive days. In the second animal model, immune competent C57BL/6 mice were infected with *M. tuberculosis* Erdman (TMCC 107). Animals were dosed b.i.d. IP with 100 mg/kg compound in 25% ethanol and 25% Solutol beginning at day 5 post-in feet ion for 10 consecutive days. Isoniazid was used as a comparative positive control and was delivered q.d. at 25 mg/kg as a positive control.

In both studies, animals were sacrificed and necropsied, bacterial burden in lungs or spleens were quantified on 7H11 agar containing carbenicillin (Sigma, C1389) and cycloheximide (Sigma, C7698) and upon incubation for three weeks bacterial colony forming units were enumerated. Outliers were identified by the Grubbs' Test and a one-way t-test at a 95% confidence interval was used to compare treatment groups and controls, to calculate p-values, and to produce bar graphs and scatter plots GraphPad Prism Version 5.0d for Mac OS X (GraphPad Software, San Diego Calif., USA www.graphpad.com).

Results.

In Vitro Potency of Lead Benzimidazoles Against Mtb H37Rv and Erdman Strains.

The discovery of a novel class of benzimidazoles that demonstrate antibacterial activity against *M. tuberculosis* and against representative clinical isolates with various drug susceptibility profiles was previously reported (Kumar et al., *J. Med. Chem.* 2011; 54:374-381). For these studies, the MIC of three lead candidates, SB-P1G10, SB-P3G2 and SB-P8B2 (FIG. 1) was confirmed against *M. tuberculosis* H37Rv and Erdman strains. SB-P8B2 and SB-P3G2 had similar MIC ranges of 0.39-0.78 μg/mL and 0.78-1.5 μg/mL, respectively, and SB-P1G10 exhibited a substantially similar MIC range of 3-6.25 μg/mL. The experimental MIC ranges of these lead compounds are therefore comparable based on typical CLSI drug guidelines. The lead benzimidazoles did not exhibit appreciable cytotoxicity against standard Vero cell line resulting in therapeutic indices of greater than 512 to 32, respectively.

Combination of SB-P8B2 with Rifampicin.

Because compounds whose mode of action is inhibition of cell division have not been evaluated for potential antagonistic interactions with currently used first line TB drugs, the lead compound with the lowest MIC, SB-P8B2, was used in combination with rifampicin as a representative of the mode of action of this novel class of compounds. This was assessed in a checkerboard in vitro growth inhibition assay (Table 1).

TABLE 1

Enhancement of drug activity (MIC)[a] with combination treatment.

| Drug | Alone | In Combination | ΣFIC[b] |
|---|---|---|---|
| [c]SB-P8B2 | 1 × MIC | 0.1 × MIC | 0.63 |
| Rifampicin | 1 × MIC | 0.5 × MIC | |

[a]MIC was determined by MABA.
[b]ΣFIC is the sum of the FICs (MIC of a drug in combination/MIC of that drug alone) for all the drugs tested in the combination. Drugs are considered synergistic when the ΣFIC is less than 0.5 and antagonistic when the ΣFIC is greater than 4.
[c]SB-P8B2 was used in combination with rifampicin as a representative of this novel class of FtsZ cell division inhibitors.

The potency of both rifampicin and SB-P8B2 was enhanced by the presence of the other, resulting in a ΣFIC of 0.63. Specifically, SB-P8B2 was 8 times more potent in the presence of rifampicin and SB-P8B2 doubled the activity of rifampicin, thus indicating that there was enhanced killing using a combination of SB-P8B2 and the first line anti-TB drug rifampicin.

In Vitro Growth Inhibition and Bactericidal Action.

Figure 2A:
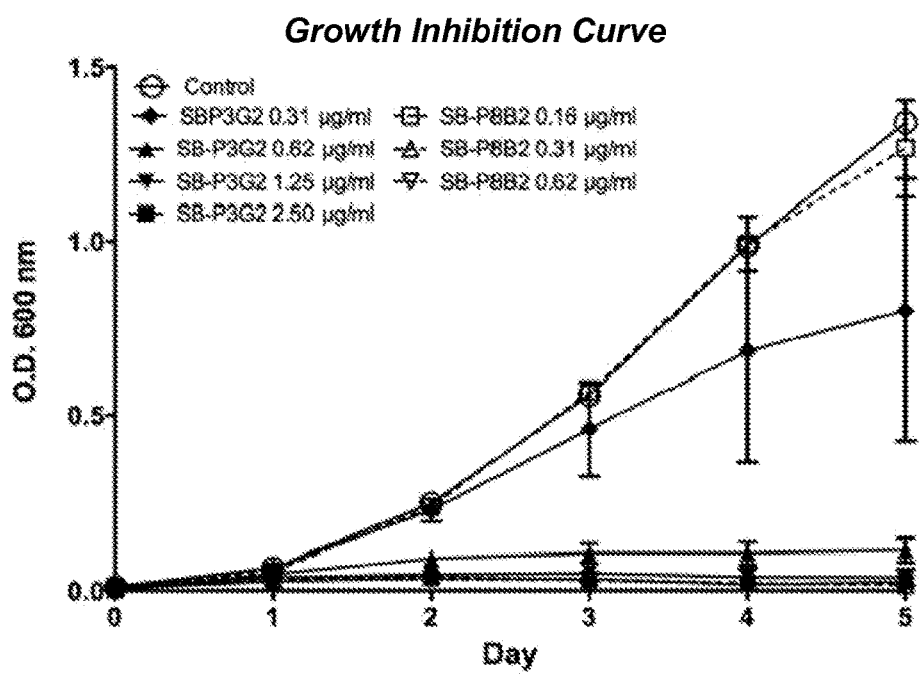
FIG. 2. (A) and (B): Growth inhibition curves. Growth inhibition curves were generated for (A) SB-P3G2 and SB-P8B2; and (B) SB-P1G10. The different concentrations were tested in triplicate and the mean and standard deviation of the O.D. 600 nm values for the different doses was plotted against time. (C) Time dose curve. A time dose curve was generated from CFU data for SB-P1G10 using different concentrations over time.
Figure 2B:
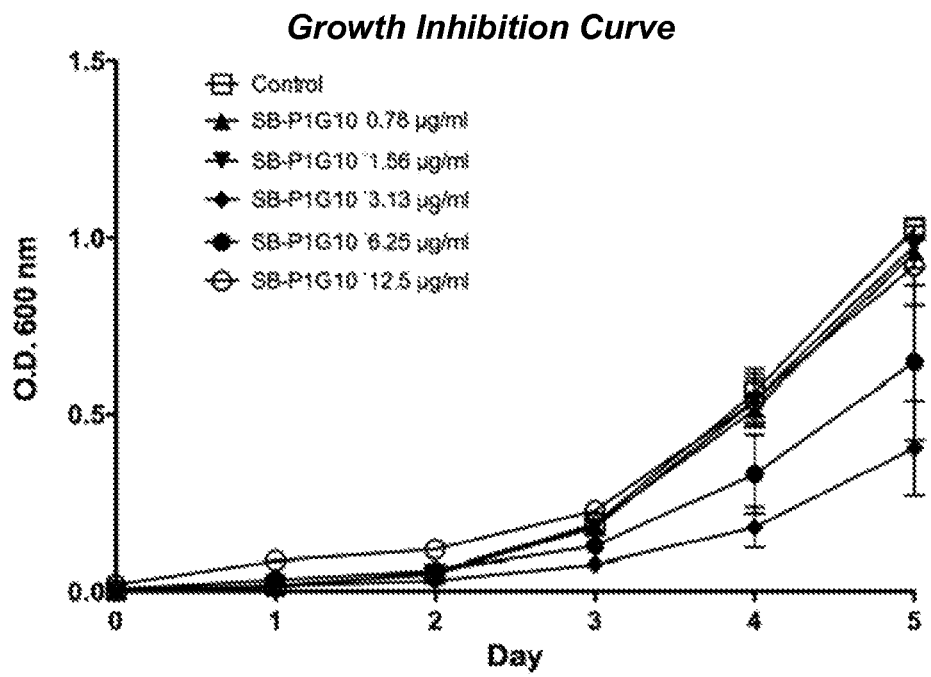
Figure 2C:
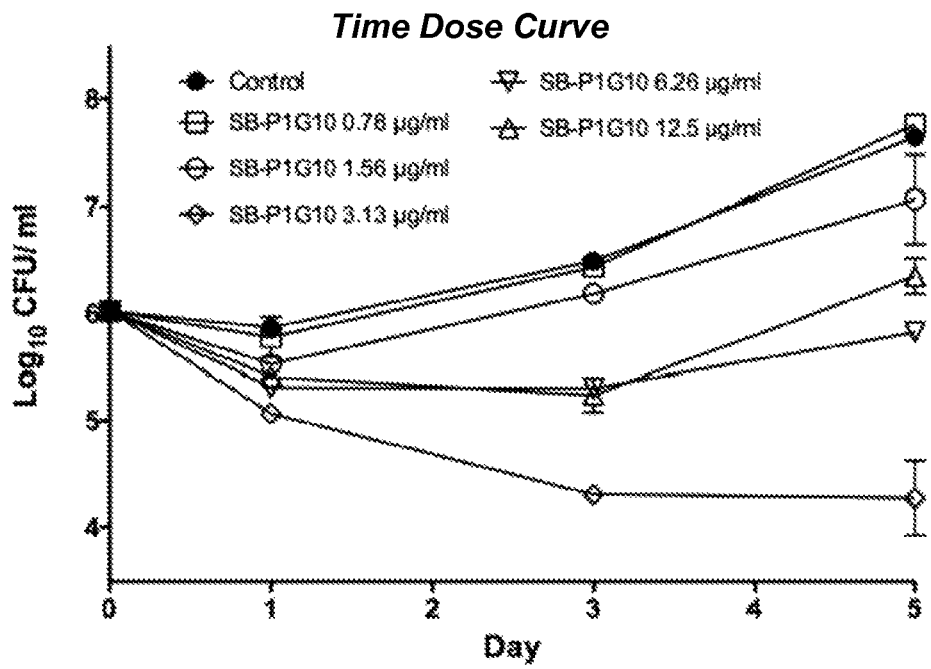

Bacterial growth was monitored in the presence of SB-P3G2, SB-P8B2 or SB-P1G10 at concentrations relative to the MIC for 5 days to evaluate the inhibition in bacterial growth rate (FIG. 2). The growth curves for the three benzimidazoles examined were all dose-dependent and not time-dependent. The growth inhibition curves for SB-P3G2 and SB-P8B2 were similar, showing that inhibition of bacterial growth correlated with increased drug concentrations (FIG. 2A). Bacterial growth was inhibited at concentrations greater than 0.62 μg/mL and 0.31 μg/mL for SB-P3G2 and SB-P8B2, respectively. In contrast, none of the concentrations tested relative to the MIC of SB-P1G10 completely inhibited bacterial growth (FIG. 2B). The bacterial growth in the presence of 0.78 μg/mL, 1.56 μg/ml, 3.13 μg/mL, 6.26 μg/mL and 12.5 μg/mL of SB-P1G10 was characterized by different rates. The SB-P1G10 O.D. 600 nm data was confirmed by plating and enumeration of CFU (FIG. 2C).

Figure 3A:
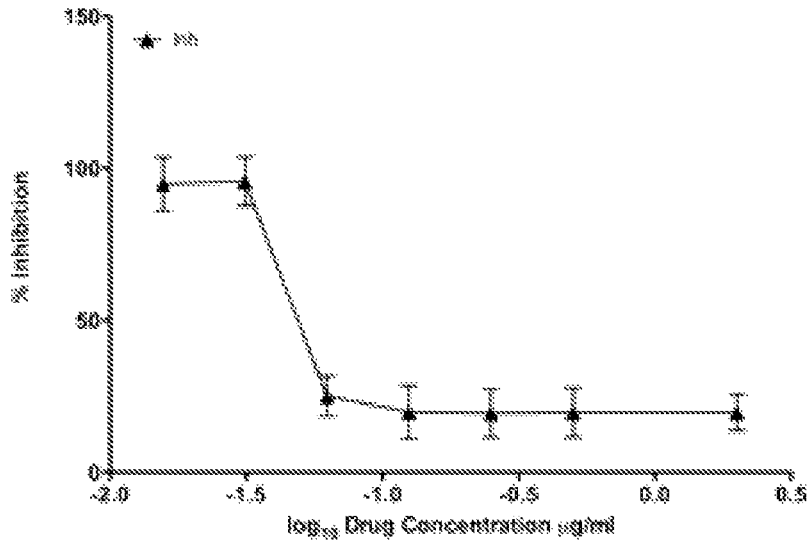
FIG. 3. Drug concentration response curves. A drug concentration response curve was generated for (A) isoniazid (Inh), which displays a sigmoidal kill curve; (B) SB-P3G2 and SB-P8B2, which display sigmoidal kill curves; and (C) SB-P1G10, which displays a narrow range of concentrations of effective bactericidal activity (NREBA) kill curve; the drug concentration response curves were generated by graphing the $\log_{10}$ drug concentrations (μg/mL) against the difference in growth between the drug-treated wells and control wells.
Figure 3B:
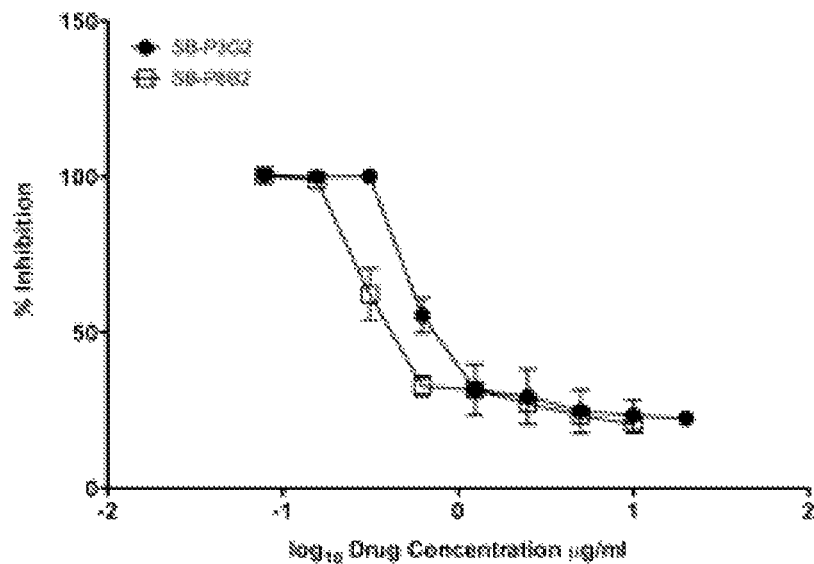
Figure 3C:
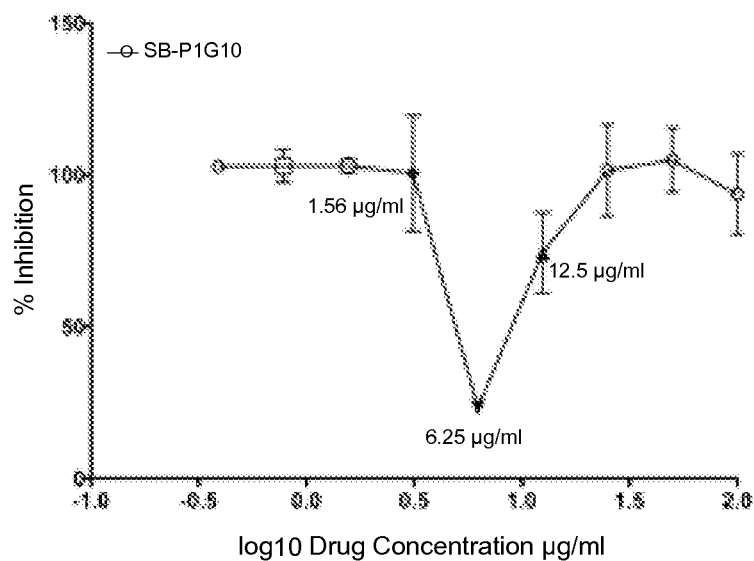

To understand the kill characteristics of SB-P3G2, SB-P8B2 and SB-P1G10, the compounds were tested for bactericidal activity at different concentrations. Bacteria treated with either SB-P3G2 or SB-P8B2 demonstrated typical sigmoidal bactericidal curves, indicating that as the compound concentration increased the percent viable bacteria decreased to a minimal population at which no additional killing was observed (FIG. 3A). In contrast, SB-P1G10 did not display a typical sigmoidal bactericidal curve. Rather, bactericidal activity was achieved in a very narrow concentration range of SB-P1G10, from 0.5-4 fold of MIC (FIG. 3B).

The resulting pronounced zonal susceptibility curve of SB-P1G10 is characteristic of the Eagle-Musselman phenomenon where optimal effective killing is centered on the MIC, and at greater concentrations the bacteria remain viable in a bacteriostatic state (Eagle and Musselman, *J. Exp. Med.* 1948; 88:99-131). To assess whether the observed kill characteristics were applicable to clinical isolates, the dose response curves for SB-P3G2, SB-P8B2 and SB-P1G10 were generated against the clinical isolates W210, NHN20, NHN382 and TN587. Notably, not only are the MIC values of each of the lead compounds against the *M. tuberculosis* clinical strains comparable to the MIC for the H37Rv laboratory strain, but the dose curves generated for each compound against the clinical isolates examined in this study and H37Rv were remarkably similar.

Activity of Select Lead Benzimidazoles Against Non-Replicating *M. tuberculosis* Grown in Low Oxygen Conditions.

As part of our ongoing efforts on the development of FtsZ inhibitors as anti-TB agents, we extended the previous study by assessing the activity of lead benzimidazoles against non-replicating *M. tuberculosis* H37Rv strain grown in low oxygen conditions. Based on the confirmed MICs against *M. tuberculosis* H37Rv and the kill-curve characteristics, SB-P3G2 and SB-P8B2 were tested for potency against non-replicating bacteria in low oxygen conditions (Table 2).

TABLE 2

In vitro potency of SB-P8B2 and SB-P3G2 against non-replicating *M. tuberculosis* grown under low oxygen conditions.

|  | $Log_{10}$ (CFU+/−SD) | $Log_{10}$ (CFU) Reduction | % Growth Reduction |
|---|---|---|---|
| Control | 5.35 ± 0.01 | na | na |
| [a]Isoniazid | 5.15 ± 0.2 | 0.2 | 36 |
| [b]Metronidazole | 4.83 ± 0.06 | 0.52 | 70 |
| [c]SB-P8B2 | 4.96 ± 0.18 | 0.39 | 59 |
| [c]SB-P3G2 | 4.80 ± 0.21 | 0.48 | 72 |

[a]Isoniazid is not effective against non-replicating bacteria.
[b]Metronidazole is effective against non-replicating bacteria but has no efficacy against actively dividing bacteria.
[c]Representative trisubstituted benzimidazoles.

Both SB-P3G2 and SB-P8B2 showed greater activity against non-replicating bacilli than isoniazid, which is known to not have potent activity against non-replicating bacteria. SB-P8B2 and SB-P3G2 at 4 µg/mL reduced the growth of *M. tuberculosis* H37Rv by 59% and 72%, respectively. Notably, SB-P3G2 reduced the growth comparable to metronidazole. In conclusion the substituted benzimidazoles SB-P3G2 and SB-P8B2 have activity against non-replicating *M. tuberculosis* resulting from low oxygen conditions.

In Vitro-In Vivo Activity Relationship.

SB-P3G2 and SB-P1G10 were used in two different animal models of acute *tuberculosis* infection to investigate the in vitro-in vivo activity relationship between lead benzimidazoles with the two disparate kill-curve characteristics. These animal models are used in our drug discovery program because they afford the ability to evaluate if a drug candidate can reduce the bacterial load during an acute infection and inhibit dissemination from the site of infection to secondary sites.

Figure 4A:
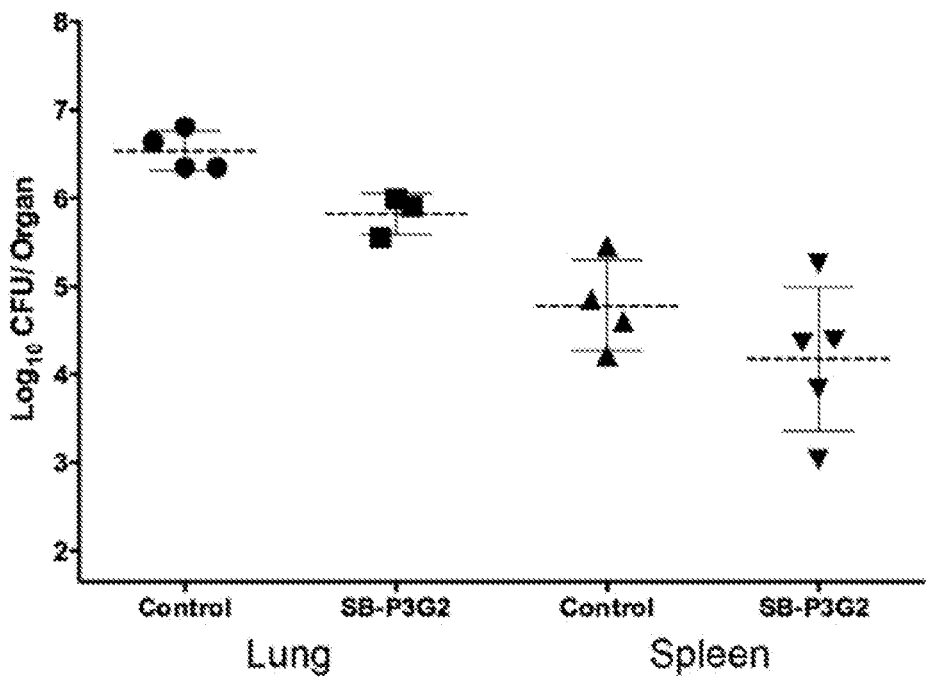
FIG. 4. Efficacy in acute animal models of *tuberculosis*. (A) Scatter plots of the bacterial CFU counts from lungs (•) and spleen (▲) from untreated control animals and the lungs (■) and spleen (▼) of infected mice after treatment with SB-P3G2 delivered IP at 150 mg/kg for 9 consecutive days to immune incompetent GKO mice. SB-P3G2 reduced the bacterial load of *M. tuberculosis* H37Rv 0.71±0.17 $\log_{10}$ CFU in the lungs and 0.41±0.36 $\log_{10}$ CFU in spleen. (B) Scatter plots of the bacterial CFU counts from spleen (▲) from untreated control animals and the spleen (▼) of infected mice after treatment with SB-P3G2 delivered IP at 100 mg/kg BID for 10 consecutive days to immune competent C57BL/6 mice. SB-P3G2 reduced the bacterial load of *M. tuberculosis* Erdman in the spleen $\log_{10}$ 1.6±0.49. In both studies, no outliers were identified by the Grubbs' Test.

In the first acute infection animal study which uses immune incompetent GKO mice, SB-P3G2 reduced the bacterial load of *M. tuberculosis* H37Rv by 0.71±0.17 $log_{10}$ CFU in the lungs and 0.41±0.36 $log_{10}$ CFU in spleen (FIG. 4A) (for methods, see Lenaerts et al., *Antimicrob. Agents Chemother.* 2003; 47:783-785). Isoniazid reduced the bacterial load 1.8 $log_{10}$ CFU in the lung and below the level of detection in the spleen.

Figure 4B:
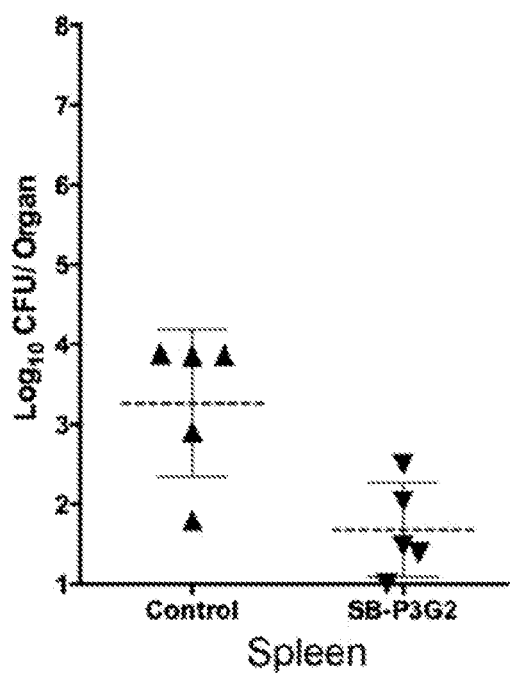

In the second dissemination model of infection using immune competent C57BL/6 mice. SB-P3G2 reduced the bacterial load of *M. tuberculosis* Erdman in the spleen by $log_{10}$ 1.6±0.49 (FIG. 4B). Isoniazid reduced the bacterial load in the lung and spleen below detectable levels. In the different animal models tested. SB-P3G2 always showed some level of detectable efficacy. Together, these animal studies show that SB-P3G2 has efficacy against an acute infection and can prevent dissemination to secondary sites. In contrast, treatment with SB-P1G10 never reduced the bacterial load in the lungs or spleen in any animal model of infection conducted. This data indicates that two of the lead benzimidazoles with similar physicochemical and in vitro potency against *M. tuberculosis*, but different in vitro inhibition kill-curve characteristics, demonstrate distinctly different efficacy outcomes.

Thus, these experiments show the in vitro-in vivo activity relationship of a lead benzimidazoles efficacy in murine models of *tuberculosis*. Selected benzimidazoles with this mode of action have activity against clinical isolates, as well as non-replicating persistent bacilli, and can enhance current therapeutic regimens.

Example 2. A Trisubstituted Benzimidazole Cell Division Inhibitor with Efficacy Against *Mycobacterium tuberculosis*

Trisubstituted benzimidazoles have demonstrated potency against Gram-positive and Gram-negative bacterial pathogens. Previously, a library of novel trisubstituted benzimidazoles were constructed for high throughput screening, and compounds were identified that exhibited potency against *M. tuberculosis* H37Rv and clinical isolates, and were not toxic to Vero cells. A new series of 2-cyclohexyl-5-acylamino-6-N,N-dimethylaminobenzimidazoles derivatives has been developed based on SAR studies. Screening identified compounds with potency against *M. tuberculosis*. A lead compound from this series, SB-P17G-A20 was discovered to have an MIC of 0.16 µg/mL and demonstrated efficacy in the TB murine acute model of infection based on the reduction of bacterial load in the lungs and spleen by 1.73±0.24 $Log_{10}$ CFU and 2.68±$Log_{10}$ CFU, respectively, when delivered at 50 mg/kg by intraperitoneal injection (IP) twice daily (bid). SB-P17G-A20 was determined to be concentration dependent and to have excellent stability in mouse and human plasma, and liver microsomes. Together, these studies demonstrate that SB-P17G-A20 has potency against *M. tuberculosis* clinical strains with varying susceptibility and efficacy in animal models of infection, and that trisubstituted benzimidazoles continue to be a platform for the development of novel inhibitors with efficacy.

Introduction.

*Tuberculosis* (TB) infects a significant portion of people worldwide resulting in the leading cause of death globally from a bacterial infection. Not all TB infections lead to active disease and in fact latent infections provide an ongoing source of infection. Despite continued efforts from the research community and clinicians, this reservoir of infection [1,2] hinders disease management efforts. Current treatment requires 6-9 months therapy with a combination of drugs; 4 drugs for 2-4 months and 2 drugs for an additional 4-5 months, and latent infections are treated with isoniazid for 6-9 months. Contributing factors hindering disease management is the aging anti-tubercular first and second line drugs, which where all discovered more than 4 decades ago, with the discovery of isoniazid in 1951, pyrazinamide in 1952, rifampin in 1957 and ethambutol in 1962, except for the very recent entry of bedaquilline in 2012, and the emergence of multi-drug resistant clinical TB strains (MDR-, XDR-TB-, TDR-TB). Further, there are concerns that the existing drug regimens even when used appropriately do not result in durable cure. Therefore, the development of next generation chemotherapeutics with a novel mode of action that can be readily incorporated into current drug regimens resulting in efficacious treatments against resistant strains, and persistent infections is a priority.

A clinically relevant drug target is generally considered to be one that is essential for infection and disease progression. Rather than pursuing drugs that target metabolic pathways and macromolecular structures of current TB drugs, the research emphasis of our drug discovery program has been septum formation and cell division protein, specifically FtsZ. Chemical inhibition and molecular approaches have substantiated FtsZ as a viable drug target in *M. tuberculosis* [3-5]. This is consistent with the work of others that have shown that FtsZ inhibition has antimicrobial activity against *M. tuberculosis* [6,7]. In addition to establishing FtsZ as a promising molecular target our studies characterizing the activity of albendazole and thiabendazole in *M. tuberculosis* demonstrate that benzimidazoles in general are an appropriate structural platform for TB drug discovery efforts [5]. Concordant with these biochemical studies our ongoing drug discovery consortium pursued the development of novel taxanes and benzimidazoles to treat TB infections [8,9]. This work led to the discovery that novel trisubstituted benzimidazoles target FtsZ with a novel mode of action [4,10,11]. Our research efforts and the work of others have established FtsZ to be a drug target in *M. tuberculosis* [4,10,11]. Further substantiating FtsZ as a clinically relevant drug target and trisubstituted benzimidazoles as a drug platform is the identified broad-spectrum activity of substituted benzamidozoles against various bacterial pathogens [4,10-12].

In our continued effort to find effective compounds against FtsZ a new series of substituted benzimidazoles has been designed and synthesized based on SAR studies on 63 compounds [10,11]. The work presented here expands on our previous reports by demonstrating the activity of the current lead compound, SB-P17G-A20, against *M. tuberculosis* H37Rv and clinical isolates and efficacy in the acute mouse model of *M. tuberculosis* infection. Time-kill curves were performed and, metabolic stability and plasma stability was determined to assess the potential in vivo pharmacokinetics and pharmacological performance of SB-P17G-A20. Together, these studies demonstrate that SB-P17G-A20 has potency against *M. tuberculosis* clinical strains with varying susceptibility and efficacy in animal models of infection, and that trisubstituted benzimidazoles continue to be a platform for the development of novel inhibitors with efficacy.

Methods.

*Mycobacterium tuberculosis* Strains, Media and Drug Conditions.

The laboratory reference strain *M. tuberculosis* H37Rv was used for standard minimal inhibitory concentrations and kill characteristics analysis [13]. *M. tuberculosis* Erdman (TMCC 107) was used in the animal model of *M. tuberculosis* infection [14,15]. Clinical isolates TN587, W210, NHN335, and NHN20 were described previously [16,17]. For in vitro assays, *M. tuberculosis* was grown in Difco™ 7H9 Middlebrook liquid media (BD Biosciences, 271310) with 10% Middlebrook OADC Enrichment (VWR, 9000-614), 0.05% Tween (G-Biosciences, 786-519), and 0.2% Glycerol at 37° C. or *M. tuberculosis* was grown on Difco™ Middlebrook 7H11 agar (BD Biosciences, 283810) supplemented with 10% OADC. For CFU assays from animal studies the agar plates were supplemented with 1% asparagine and carbenicillin 50 mg/L (Sigma, C1389) and cycloheximide 10 mg/L (Sigma, C7698). Mutant selection studies were performed on solid medium containing drug candidate relative to experimentally determined MIC.

SAR-based drug design was used to develop a new series of 6-N,N-dimethylamine next generation trisubstituted benzimidazoles [10,11]. Metronidazole (Sigma cat# M1547), rifampicin (Sigma cat #83907), isoniazid (INH), SB-P17G-C2 and SB-P17G-A20, used in in vitro assays were dissolved in DMSO. Isoniazid was dissolved in water, filter sterilized and delivered IP in animal studies. The benzimidazole SB-P17G-A20 was dissolved in a 25% Solutol, 25% Ethanol in PBS diluent and delivered IP to animals.

In Vitro Growth Assays of Treated Bacteria.

MIC values for the benzimidazole SB-P17G-A20 against *M. tuberculosis* and the clinical isolates were determined using a modified 96-well microplate Alamar Blue assay (MABA) [10,18]. Three independent experiments were performed for the MICs and the standard error of the mean was calculated. A dose response curve with standard errors was generated for SB-P17G-A20 by graphing the $\log_{10}$ drug concentrations against the difference in growth between the treated bacteria and control bacteria from three independent experiments using GraphPad Prism Version 5.0d for Mac OS X (GraphPad Software, San Diego Calif., USA, www.graphpad.com). Briefly, culture tubes were inoculated with *M. tuberculosis* H37Rv $OD_{600\ nm}$ 0.010, followed by the addition of the compound at different concentrations. The bacteria were grown at 37° C. and readings were taken every 24 h for 7 days. The mean and standard error (SE) for the $OD_{600\ nm}$ values were plotted against time using GraphPad Prism Version 5.0d for Mac OS X (GraphPad Software, San Diego Calif., USA, www.graphpad.com). At day 0, 2, 4 and 6 aliquots were removed from each culture, dilution series were made and plated for CFUs. The mean and SE for the CFU values were plotted against time using GraphPad Prism Version 5.0d for Mac OS X (GraphPad Software, San Diego Calif., USA, www.graphpad.com). MIC values of SB-P17G-C2 against clinical isolates (0.06-0.13 µg/mL) were determined and reported [11].

In Vitro Combinatorial Drug Studies.

A checkerboard in vitro 96 well plate method was used to examine possible antagonism between the SB-P17G-A20 and rifampicin. Briefly, each was diluted in a 96 well plate in a checkerboard pattern, bacteria were added and the plates were incubated at 37° C. Alamar Blue was added at day 6 and the plates were read 24 h later. The Fractional inhibitory concentration (FIC) is defined as the MIC of a drug in combination divided by the MIC of that drug alone and the fractional inhibitory index (FICI) is the sum of the FIC's (ΣFIC) for the drugs tested in the combination [19]. When the ΣFIC is less than 0.5 the drugs are considered synergistic, when the ΣFIC is between 0.5 and 4 there is no enhanced activity, and when the ΣFIC is greater than 4 the drugs are antagonistic.

Mtb FtsZ Protein Preparation.

*E. coli* expression plasmid encoding the ftsz gene (pET 15b vector) was transformed into 100 µL of BL21(DE3) cells. The transformed cells were plated onto LB plates, containing 100 µg/mL ampicillin. The antibiotic concentration was kept the same for the following steps. The plates were incubated overnight at 37° C. The colonies were picked and grown in 10 mL of LB media at 37° C. at 250 rpm shake rate. The inoculum was transferred to 1 L of LB media in a 4 L flask and grown to an OD of 0.6 at A600. Then, 1 mM IPTG was added to induce protein expression overnight at 25° C. at 250 rpm shake rate. Next day the cells were harvested at 5K rpm for 15 min and re-suspended in approximately 20-30 mL binding buffer (500 mM NaCl, 20 mM sodium phosphate, pH 7.8). The re-suspended cells were lysed using cell disruptor. The lysate was centrifuged in an ultracentrifuge at 33K rpm, 4° C. for 90 min. The supernatant was filtered and loaded onto a $Ni^{2+}$-NTA column washed with 50 mL of binding buffer and eluted using a gradient of binding buffer with 30-500 mM imidazole. The eluted protein was first dialyzed against the polymerization buffer (50 mM MES, 5 mM $MgCl_2$, 50 mM KCl pH 6.5) and then polymerization buffer containing 10% v/v glycerol. The protein was then concentrated and stored at −80° C. for further use. Since the aromatic residues in Mtb FtsZ protein are low (Tyr: 1, Trp: 0), it is not reliable to follow the concentration of protein by scanning at A280. The concentration of protein was therefore ascertained using the Bradford kit from Sigma.

Transmission Electron Microscopy (TEM) Analysis.

A stock solution of compound SB-P17G-A20 was prepared in ethanol. *M. tuberculosis* FtsZ (5 μM) was incubated with 40 or 80 μM of compound SB-P17G-A20 in the polymerization buffer (50 mM MES, 5 mM MgCl$_2$, 100 mM KCl pH 6.5) for 15 min on ice. To each solution was added GTP to the final concentration of 25 μM. The resulting solution was incubated at 37° C. for 30 min. The incubated solution was diluted 5 times with the polymerization buffer and immediately transferred to carbon coated 300 mesh formvar copper grid and negatively stained with 1% uranyl acetate. The samples were viewed with a FEI Tecnai 12 BioTwinG transmission electron microscope at 80 kV. Digital images were acquired with an AMT XR-60 CCD digital camera system.

Plasma Stability Studies in Human and Mouse Plasma.

Blood was collected from animals using lithium heparin as anticoagulant, in the ARW Domain at DSAR Montpellier (371 rue du Pr. J. Blayac, 34184 Montpellier Cedex 04, France) or vendors such as Charles River. Human plasma using lithium heparin as anticoagulant was provided by the EFS (Etablissement Français du Sang) of Montpellier, France. Plasma was spiked with the compound in order to obtain a final drug concentration of 100 ng/mL (expressed as non-salified compound). The spiked plasma (dedicated to C1h and C4h) was then incubated at 37° C. for 1 h and 4 h. Plasma samples were analyzed by LC-MS/MS following protein precipitation. The limit of quantification for compounds was 10 ng/mL.

Chromatographic Conditions for LC Analysis:

10 μL of the sample was injected to Luna Phenomenex C8 (50 mm×2.0 mm, 3 μm). Solvent A: ammonium acetate (0.15 g)/formic acid (2 mL)/HPLC water up to 1000 mL. Solvent B: ammonium acetate (0.15 g)/formic acid (2 mL)/Methanol (200 mL)/Acetonitrile up to 1000 mL, flow rate of 0.3 mL/min, t=0-6 min. gradient of 10-90% of B. Retention time for SB-P17G-C2 was 1.85 min and for SB-P17G-A20 was 3.3 min. MS/MS condition used for detection: Finnigan TSQ Quantum disco instrument, Excalibur version 2.0 acquisition system, ESI positive ion ionization mode. The mean percent of difference between C1h or C4h and C0 concentrations was calculated.

$$M \% D (\%) = 100 \times [(C1h \text{ or } C4h) - C0]/C0$$

The compounds were considered as stable if the mean percent of difference between C4h and C0 concentrations was less than 20%.

Evaluation of Oxidative Metabolic Lability in Mouse/Human Liver Microsomes.

Microsomal fractions were prepared in the Drug Disposition Domain at DSAR Montpellier (371 rue du Pr. J. Blayac, 34184 Montpellier Cedex 04, France). SB-P17G-C2 or SB-P17G-A20 at 5 μM concentration was incubated with microsomal proteins (human or mouse, 1 mg/mL) in an incubation buffer containing phosphate 0.1 M, pH 7.4 and 1 mM NADPH as cofactor for cytochrome P-450 (CYP). The flavin-containing monooxygenases (FMO)-dependent reactions were run in the presence of bovine serum albumin (BSA, 0.1%) for the duration of 0 and 20 min (with or without microsomal proteins and/or cofactors). Enzyme activity was stopped with one volume of acetonitrile containing the internal standard, dextromethorphan. Following protein precipitation with acetonitrile and their removal by centrifugation, supernatant fluids were analyzed by LC/MS-MS.

Chromatographic Conditions for LC Analysis.

SB-P17G-A20: 5 μL of the sample was injected to Hypersil Gold Thermo C18 (50 mm×2.1 mm, 1.9 μm), Solvent A: ammonium acetate (0.08 g)/formic acid (2 mL)/HPLC water up to 1000 mL. Solvent B: ammonium acetate (0.08 g)/formic acid (2 mL)/methanol (200 mL)/acetonitrile up to 1000 mL, flow rate of 0.5 mL/min, t=0-3 min, gradient of 10-100% of B. Retention time for SB-P17G-A20 was 1.52 min.

SB-P17G-C2: 10 μL of the sample was injected to Kinetex C18 (30 mm×2.1 mm, 2.6 μC), Solvent A: HPLC-grade water up to 1000 mL, formic acid (0.1%). Solvent B: acetonitrile up to 1000 mL, formic acid (0.1%); flow rate of 0.75 mL/min, t=0-1.5 min, gradient of 5-95% of B. Retention time for SB-P17G-C2 was 0.73 min.

MS/MS Condition Used for Detection.

Thermo Finnigan TSQ Quantum Ultra instrument, ESI positive ion ionization mode. Each compound is studied in duplicates. Results are expressed in percentage of lability (or total metabolism).

$$\text{Total metabolism} = [1 - (\text{UC\_Peak Area} + \text{Cofactor at } T20) / (\text{UC\_Peak Area Reference at } T0)] \times 100$$

UC=Unchanged Compound; "Reference" sample was NADPH for liver microsomal preparation Modified Rapid Murine Model.

Modifications were made to the short term model. Briefly, *M. tuberculosis* strain Erdman was delivered to C57BL/6-Ifngtm1ts (Jackson Laboratories, Bar Harbor, Me.) by aerosol using a Middlebrook aerosol generation devise (GlasCol, Terre Haute, Ind.). Treatments were given days 5 to 14 post-infection. INH was delivered IP 20 mg/kg qd and SB-P17G-A20 was delivered 50 mg/kg IP bid. Controls were infected and treated with vehicle only bid. Animals were sacrificed day 15 post-infection and the lungs and spleens were harvested. The organs were homogenized in saline, diluted, and plated. Bacterial colonics were counted, the colony counts were converted to logarithms and outliers were identified by the Grubbs' Test using an online calculator (GraphPad Software, San Diego Calif., USA www.graphpad.com). The one-way t-test at a 95% confidence interval, using GraphPad Prism Version 5.0d for Mac OS X (GraphPad Software, San Diego Calif., USA www.graphpad.com), was used to compare treatment groups and infected controls, to calculate p-values, and to produce scatter plots.

Ethics Statement.

All use of vertebrate animals at Colorado State University is conducted under AAALAC approval and has an OLAW number of A3572-01. Animals are housed in a state-of-the art ABL-3 facility that is supervised by full-time staff veterinarians and a large number of support staff. The CSU animal assurance welfare number is A3572-01 under file with the NIH. Veterinary care is consistent with the recommendations of the American Veterinary Medical Association (AVMA) Guidelines.

Results.

Optimized Compound SB-P17G-A20 has Activity Against *M. tuberculosis* Clinical Isolates and Low Spontaneous Resistant Frequency.

Figure 6:
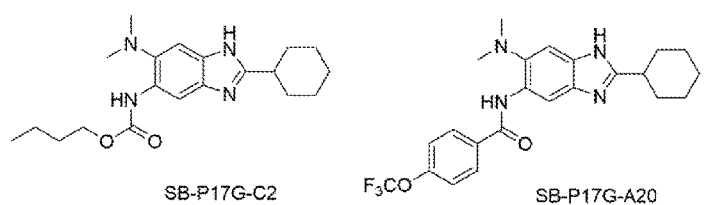
FIG. 6. Chemical structures of certain 2,5,6-trisubstituted benzimidazoles.

Previously we reported that select benzimidazoles demonstrated activity against *M. tuberculosis* H37Rv and representative clinical isolates with different susceptibilities to therapeutic *tuberculosis* drugs [10,11]. Based on the SAR studies on 63 compounds, we identified several 2-cyclohexyl-5-acylamino-6-N,N-dimethylaminobenzimidazoles with MIC in the range of 0.06-0.63 µg/mL [11]. The two most active compounds, SB-P17G-C2 and SB-P17G-A20 (FIG. 6) with MIC 0.06 and 0.16 µg/mL, respectively, were selected as leads. The MIC for SB-P17G-A20 against different clinical stains of *M. tuberculosis* is 0.16 µg/mL, demonstrating that SB-P17G-A20 is equally potent against drug-sensitive and drug-resistant strains of *M. tuberculosis* (Table 2.1).

TABLE 2.1

Susceptibility of *M. tuberculosis* strains to SB-P17G-A20.

| | *Mycobacteria tuberculosis* strains | | | | |
|---|---|---|---|---|---|
| | H37Rv µg/mL | TN587 µg/mL | NHN382 µg/mL | W210 µg/mL | NHN20 µg/mL |
| SB-P17G-A20 | 0.16 | 0.16 | 0.16 | 0.16 | 0.16 |

Figure 7:
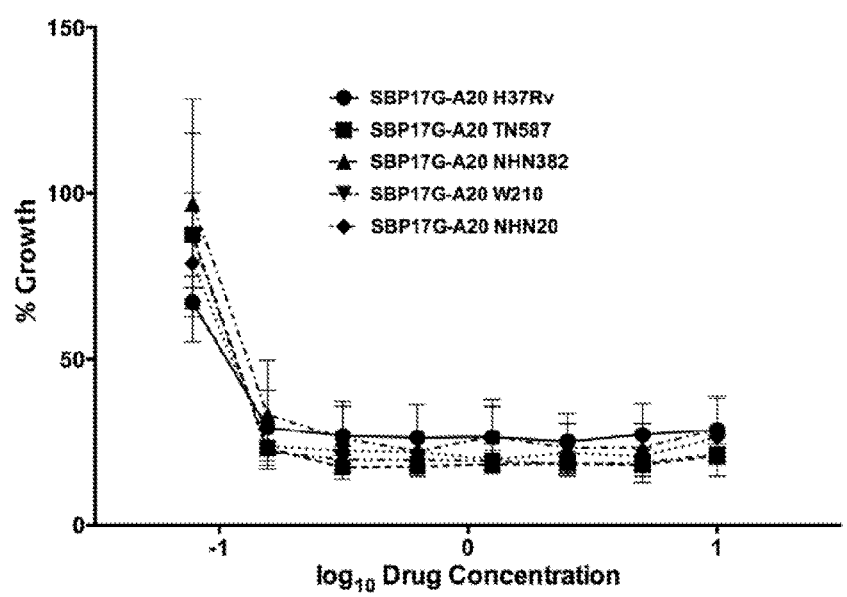
FIG. 7. Activity of SB-P17G-A20 against *M. tuberculosis* clinical isolates. Dose response curves were generated from MABA data for *M. tuberculosis* strains (H37Rv, TN587, NHN382, W210 and NHN20) treated with SB-P17G-A20. The curves were generated by graphing the $\log_{10}$ drug concentrations against the difference in growth between the drug treated wells and control wells using GraphPad Prism Version 5.0d for Mac OS X (GraphPad Software, San Diego Calif., USA, www.graphpad.com).

The growth of *M. tuberculosis* in the presence of SB-P17G-A20 was sigmoidal indicating that as the compound concentration increased the viable bacteria decreased until a concentration was reached where no additional killing was detected (FIG. 7). Similarly, dose curves for the clinical isolates treated with SB-P17G-A20 were generated and superimposed on the same graph with the dose curve generated for *M. tuberculosis* H37Rv to further demonstrate that there were no differences in the kill characteristics between the different *M. tuberculosis* strains and clinical isolates. Together, the MIC values and inhibitory characteristics of SB-P17G-A20 were also similar for each strain regardless of resistance status indicating that there are no inherent cross resistance concerns (FIG. 7).

To further assess potential drug resistance issues with the benzimidazole drug class or FtsZ inhibitors in general, *M. tuberculosis* H37Rv ($2 \times 10^9$ cells) was plated on 1.6 µg/mL of SB-P17G-A20, which is 10 times the experimentally determined MIC. This approach determines the probability that a mutation is present in the bacterial population that provides a selective advantage in the presence of the drug thereby conferring resistance. It does not account for resistance that arises due to many mutation events selected for in a single cell. No mutants where observed, and no single resistant colony was obtained.

SB-P17G-A20 Inhibits FtsZ Polymerization.

Figure 8:
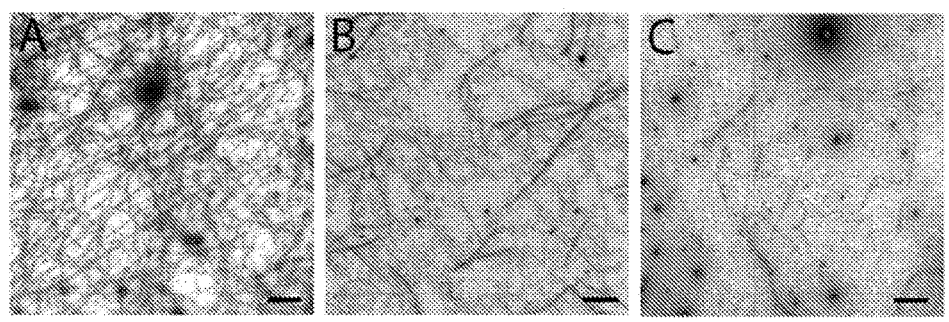
FIG. 8. Transmission Electron Microscopy of FtsZ. FtsZ (5 μM) was polymerized by GTP (25 μM) in the absence (A) and presence of SB-P17G-A20 at 40 μM (B) and 80 μM (C). Images are at 49.000× magnification (scale bar 500 nm).

Transmission electron microscopy (TEM) imaging of Mtb FtsZ treated with SB-P17G-A20 demonstrated the ability of the compound to inhibit polymerization and aggregation. Mtb FtsZ (5 µM) treated with SB-P17G-A20 at 40 µM and 80 µM concentration following addition of GTP (25 µM) formed fewer, shorter and thinner FtsZ polymers when compared to the untreated protein. In the absence of inhibitor, Mtb FtsZ formed a dense network of long polymers, which tend to aggregate (FIG. 8A) while in the presence of 40 µM SB-P17G-A20, the length, density and aggregation was visibly reduced (FIG. 8B), and the effect is more apparent at 80 µM treatment where dispersed FtsZ polymers are observed (FIG. 8C). These studies confirm that FtsZ is the molecular target of SB-P17G-A20, which is consistent with our previous report for the mode of action for substituted benzimidazoles [11].

Plasma Stability and Metabolic Liability of SB-P17G-A20 and SB-P17G-C2.

Compounds with poor plasma stability often have short $t_{1/2}$, and high clearance. To assess the potential in vivo pharmacokinetics (PK), the stability of SB-P17G-A20 and SB-P17G-C2 were evaluated in the presence of human and mouse plasma. SB-P17G-A20 and SB-P17G-C2 were found to be stable in human plasma with only 0.1% and 6.1% hydrolysis, respectively after 4 h of incubation (Table 2.2). SB-P17G-C2 was highly unstable in mouse plasma being hydrolyzed 87.6% after a 4 h incubation (Table 2.2). In contrast, SB-P17G-A20 was found to be stable in mouse plasma with only 24.4% hydrolysis after a 4 h incubation.

TABLE 2.2

Plasma stability and liver microsome lability of SB-P17G-C2 and SB-P17G-A20.

| | Plasma Stability (% hydrolysis) | | Liver Microsome Lability | |
|---|---|---|---|---|
| Compound | Human (4 h) | Mouse (4 h) | Human | Mouse |
| SB-P17G-C2 | 6.1 | 87.6 | 90% | 96% |
| SB-P17G-A20 | 0.1 | 24.4 | 39% | 45% |

Metabolic stability is also often a major limitation for lead drug candidates. To assess the extent of metabolic conversion SB-P17G-A20 and SB-P17G-C2 were evaluated using a microsomal stability assay. SB-P17G-C2 was found to be highly labile with 90% and 96% conversion in the presence of human and mouse liver microsomes, respectively (Table 2.2). In comparison, SB-P17G-A20 exhibited only moderate lability in the presence of liver microsomes with 39% conversion in human liver microsomes and 45% conversion in mouse liver microsomes (Table 2.2). These data along with previously published toxicity results [11] indicate that SB-P17G-A20 has much more favorable physiochemical properties than SB-P17G-C2 and is considered the lead benzimidazole candidate.

Killing Characteristics of SB-P17G-A20 Against Whole Bacteria.

Figure 9:
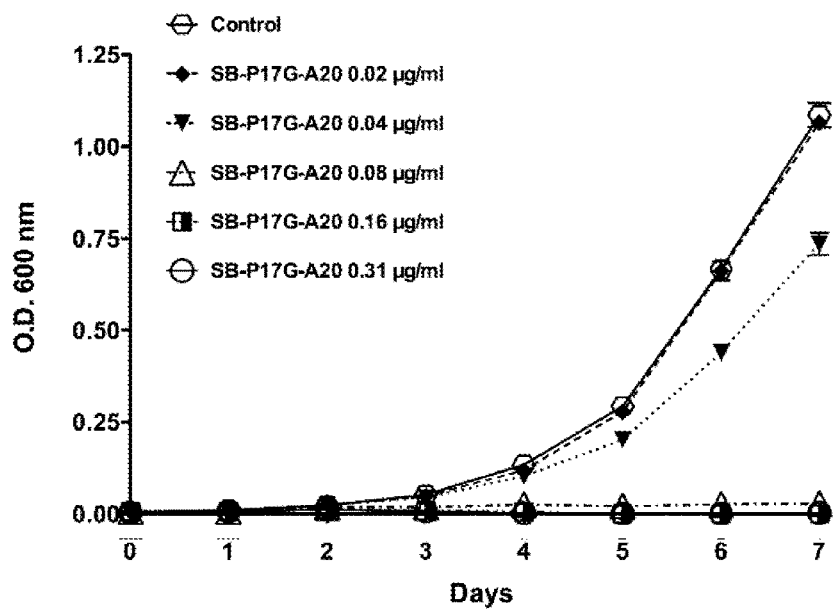
FIG. 9. Killing characteristics of SB-P17G-A20 against whole bacteria. The time dose curves were generated from $OD_{600\ nm}$ (A) and from CFU enumeration (B) data. Different concentrations of the compound were tested in triplicate and the mean and standard deviation of the $OD_{600\ nm}$ values or the CFU counts from Day 0, 2, 4, and 6 were plotted against time using GraphPad Prism Version 5.0d for Mac OS X (GraphPad Software, San Diego Calif., USA, www.graphpad.com).
Figure 9:
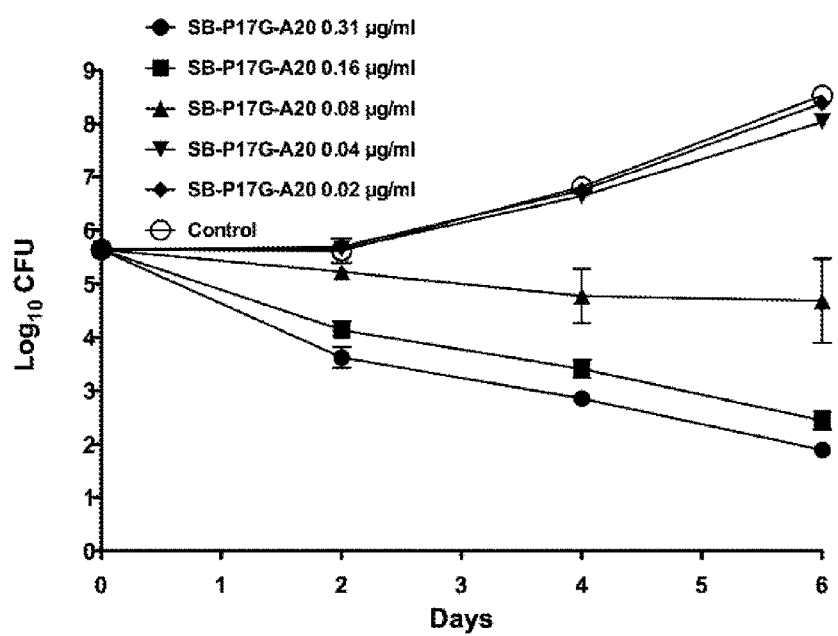

To investigate the killing characteristics of SB-P17G-A20, bacterial growth in the presence of different concentrations of the compound was monitored by OD600 nm and bactericidal effect was monitored over 7 days (FIG. 9A, B). The growth curve of *M. tuberculosis* in the presence of various concentration of SB-P17G-A20 showed that this is a concentration dependent inhibitory agent. *M. tuberculosis* did not grow in the presence of SB-P17G-A20 at concentrations near the MIC. Notably, bacterial growth was affected by sub-MIC concentrations ranging from 0.16 µg/mL to 0.02 µg/mL (FIG. 9A). Similarly, the viability of *M. tuberculosis* as determined by plating and outgrowth is also reduced at concentrations of SB-P17G-A20 below the MIC. SB-P17G-A20 at 0.08 µg/mL steadily reduced bacterial viability with concentrations of 0.16 µg/mL to greater than the MIC having an increased impacted (FIG. 9B). Together, these data indicate that the FtsZ cell division protein inhibitor SB-P17G-A20 is a concentration-dependent inhibitor with sub-MIC inhibitory characteristics.

SB-P17G-A20 is not Antagonistic with the First Line Antitubercular Rifampicin.

As part of our TB drug discovery program we assessed the combinatorial activity of lead drug candidates and a selected front-line TB drug. We evaluated SB-P17G-A20 in the presence of rifampicin and found that SB-P17G-A20 activity against *M. tuberculosis* was enhanced 2-4 fold in the presence of rifampicin and rifampicin activity against *M. tuberculosis* was enhanced 2 fold by the presence of SB-P17G-A20. The resulting ΣFIC for rifampicin in combination with SB-P17G-A20 was 0.75 indicating that these drugs are not antagonistic and therefore could be used in combination to treat a TB infection. This result along with our previous results confirm that benzimidazoles in general are not antagonistic with one of the front-line clinical drugs and, in fact enhance the activity of rifampicin against *M. tuberculosis* between 2 and 4 fold.

SB-P17G-A20 Demonstrates Efficacy in a *Tuberculosis* Murine Model of Infection.

Figure 10:
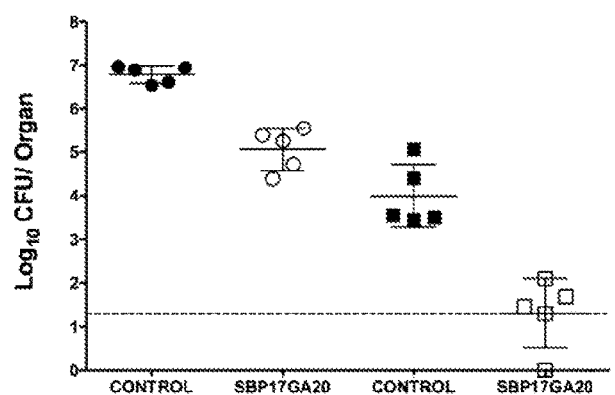
FIG. 10. (A) Efficacy of SB-P17G-A20 in a *tuberculosis* murine model of infection. Scatter plot of the CFU counts from the lung and spleens of infected mice after drug therapy with SB-P17G-A20 delivered IP at 50 mg/kg bid. The colony counts were converted to logarithms. The lower level of detection was 1 $\log_{10}$ CFU. Outliers were identified by the Grubbs' Test using an online calculator (GraphPad Software, San Diego Calif., USA www.graphpad.com). A scatter plot of the CFU data from the lung and spleens of individual mice from the treatment and control groups were plotted with the mean and SE from each group using GraphPad Prism Version 5.0d for Mac OS X (GraphPad Software, San Diego Calif., USA www.graphpad.com). (B) IP data for SB-P17G-A20. (C) PO data for SB-P17G-A20. L=lung; S=spleen. Thus, bacterial response to treatment influences susceptibility. Drug candidates with sigmoidal kill curves demonstrate efficacy in the mouse model of infection, whereas candidates that have a bimodal 'narrow zone' of kill do not. Candidates identified by the screens described herein have enhanced efficacy in the mouse model of infection: they reduce bacterial load in the spleen to below levels of detection or prevent dissemination, comparable to isoniazid.
Figure 10:
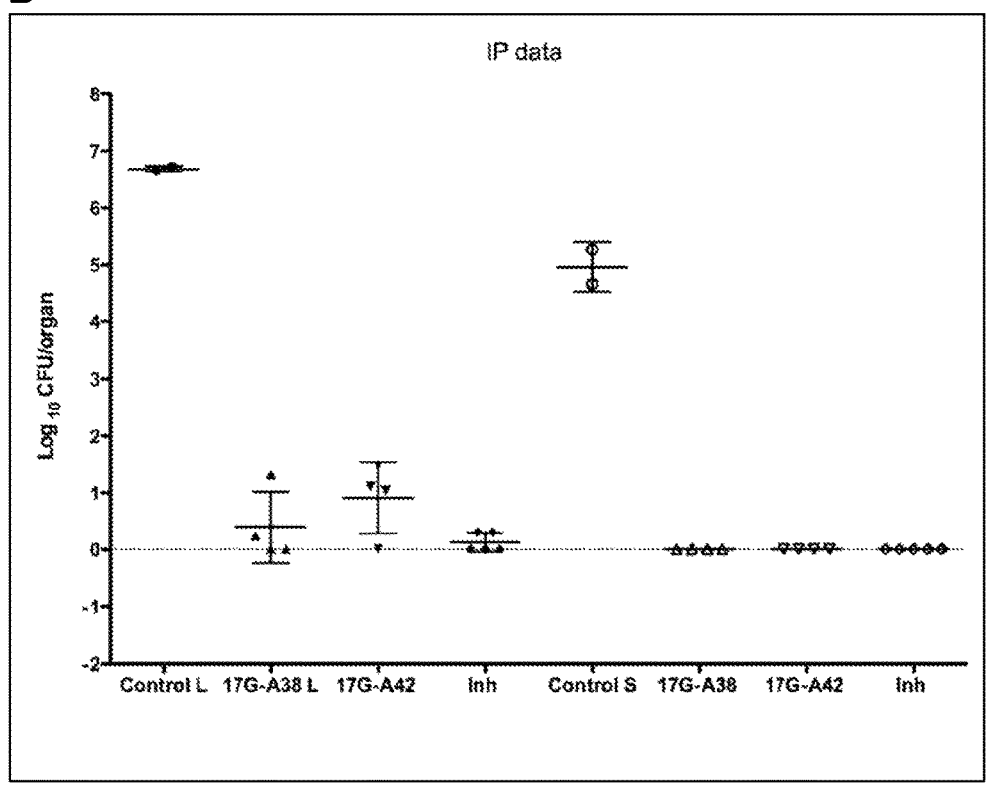
Figure 10:
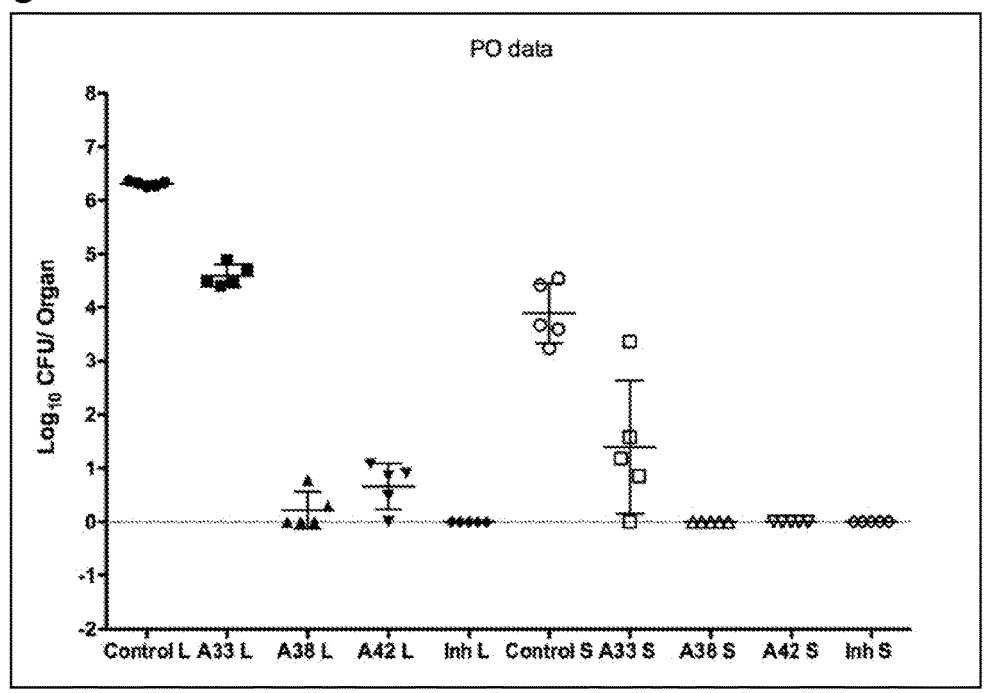

To assess the efficacy of SB-P17G-A20, it was delivered 50 mg/kg IP bid in a rapid acute murine model of infection (FIG. 10). INH was delivered IP 20 mg/kg qd as a control and reduced the CFU counts in the lung and spleen below the level of detection for this experiment. In this acute model, all mice treated with SB-P17G-A20 had bacterial counts in the lung less than untreated infected controls resulting in a reduction in the bacterial load in the lungs of 1.73±0.24 $\log_{10}$ CFU (p value <0.0001). Similarly, all treated mice with SB-P17G-A20 had bacterial counts in the spleen lower than the untreated infected controls, and 1 mouse had no detectable bacteria at the lowest level of detection, resulting in a reduction of 2.68±0.48 $\log_{10}$ CFU (p value 0.0002) bacterial load in the spleen. However, when SB-P17G-C2 was assessed for efficacy, there was no significant reduction in the bacterial load in the lungs or spleen (data not shown). This is consistent with the plasma and metabolic stability of SB-P17G-A20 and SB-P17G-C2. It is important to note that SB-P17G-A20 is the first lead compound in this class that has significantly reduced the bacterial load in both the lung and spleens.

Discussion.

*M. tuberculosis* continues to be one of the leading causes of death due to an infectious disease. The emergence of *M. tuberculosis* strains that are resistant to frontline TB drugs and therefore TB drug combinations has hampered the management and control of this disease. As part of our drug discovery program, we previously developed and identified several lead substituted benzimidazoles, SB-P3G2, SB-P8B2 and SB-P1G10, which demonstrated similar antibacterial activity against *M. tuberculosis* and clinical isolates with different resistant profiles [10]. SB-P3G2 was well-characterized and was shown to inhibit FtsZ polymerization in a dose dependent manner and increase the GTPase activity that promotes FtsZ polymerization and the formation of FtsZ polymers [10]. Since the compounds, SB-P3G2 and SB-P8B2 have shown promising antibacterial activities in vitro and in vivo, we continued optimization of substituted benzimidazoles through systematic structural modifications based on SAR studies. This resulted in the development of a series of 2-cyclohexyl-5-acylamiono-6-N,N-dimethylamino-benzimidazoles with MICs in the range of 0.06-0.63 μg/mL against *M. tuberculosis* and clinical isolates with different resistance profiles [11]. From this series, SB-P17G-C2 and SB-P17G-A20 where identified as interesting lead compounds with MIC values of 0.06 μg/mL and 0.16 μg/mL, respectively.

SB-P17G-A20 has activity against *M. tuberculosis* H37Rv and clinical isolates with different resistance profiles, which is consistent with our previous results with this structural class of compounds, such as SB-P17G-C2 [11]. SB-P17G-A20 is equally effective against *M. tuberculosis* and clinical isolates over a wide concentration range. This is important because it shows that SB-P17G-A20 is bacteri-cidal against existing clinical strains and at pharmacologically achievable concentrations. Notably, it was observed that in some cases bacterial growth was reduced by SB-P17G-A20 at concentrations as low as 0.125×MIC. To evaluate the potential use of SB-P17G-A20 in combination frontline clinical drugs, SB-P17G-A20 was tested in combination with rifampicin. This revealed that SB-P17G-A20 was enhanced by the presence of rifampicin and enhanced the activity of rifampicin, thus allowing these two drug classes to be used in combination.

We were unable to select for SB-P17G-A20 spontaneous resistant mutants of *M. tuberculosis*. Development of resistant mutants was attempted by independent selection and growth of *M. tuberculosis* H37Rv. As *M. tuberculosis* exhibits low genetic diversity in general, this result is not surprising. In addition, the inability to derive high-level resistant mutants is consistent with our previous molecular studies with dominant-negative temperature sensitive FtsZ merodiploid strains of *M. tuberculosis* [3]. These studies demonstrated that mutations in FtsZ resulted in changes in protein structure and GTPase activity, which adversely affected FtsZ polymerization resulting in the dominant-negative phenotype. The observed dominant-negative phenotype did not require a large number of inactive temperature sensitive FtsZ proteins. Rather, only a few inactive FtsZ proteins can result in molecular poisoning because of the fact that FtsZ must undergo a successful polymerization event to perform its structural role. Accordingly, the failure to select for high-level resistance to SB-P17G-A20 can be attributed to the inability of FtsZ to tolerate structural changes or amino acid changes in the GTPase domain.

Because unstable compounds have short $t_{1/2}$ and high clearance, and therefore poor pharmacological performance, it was necessary to determine the in vivo pharmacokinetic properties of SB-P17G-C2 and SB-P17G-A20 assessing plasma stability and metabolic stability in liver microsomes. While both compounds were stable in human plasma studies using mouse plasma revealed that SB-P17G-C2 is hydrolyzed 90% in 4 h. The significant difference in plasma stability results from the carbamate moiety at the 5-position of SB-P17G-C2, which is an amide group in SB-P17G-A20 that is more resistant to hydrolysis. Similarly, the conversion rate of SB-P17G-A20 was significantly slower than SB-P17G-C2 in the presence of liver microsomes. These data indicate that SB-P17G-A20 has much better in vivo pharmacokinetic properties than SB-P17G-C2.

Based on the potency and the kill-curve characteristics, along with the stability data, SB-P17G-A20 was advanced to efficacy studies using an acute mouse model of infection to assess potential as a lead compound. In this model SB-P17G-A20 significantly reduced the bacterial load in both the lungs and the spleen. In particular. SB-P17G-A20 cither killed the bacteria upon dissemination or within the spleen because the bacteria recovered from the spleen following treatment where at the lowest level of detection if detectable at all. SB-P17G-C2 was also evaluated for efficacy in an acute mouse model of infection. However, this compound did not significantly reduce the bacterial load in the lungs or spleen, which is attributed to its poor stability in mouse plasma and microsomes. Thus far, SB-P17G-A20 is the most potent trisubstituted benzimidazoles developed and tested in the animal model of infection as determined by the overall reduction in the bacterial load in the lungs and spleen.

Conclusion.

The optimized substituted benzimidazole, SB-P17G-A20, was characterized in vitro and in vivo for potency against *M.* tuberculosis clinical strains and efficacy in a *M. tuberculosis* murine model of acute infection. In vitro studies have revealed that SB-P17G-A20 has activity against strains with various drug susceptibility profiles is concentration-dependent, and possesses bactericidal activity at sub-MIC concentrations. In addition, SB-P17G-A20 is not antagonistic to the front-line TB drug rifampicin, providing the opportunity to be used in combination therapies. SB-P17G-A20 showed much better plasma/metabolic stability than other lead candidates and although the efficacy of SB-P17G-A20 in a chronic model of infection has not been performed yet, the demonstrated efficacy in an acute infection model substantiates that the 2,5,6-trisubstituted benzimidazole scaffold is a platform for the discovery and development of antitubercular drugs.

CITATIONS

1. Raviglione M C, Smith I M (2007) XDR *tuberculosis*—implications for global public health. N Engl J Med 356: 656-659.
2. Migliori G B, De Iaco G, Besozzi Ci, Centis R, Cirillo D M (2007) First *tuberculosis* cases in Italy resistant to all tested drugs. Euro Surveill 12: E070517 070511.
3. Respicio L, Nair P A, Huang Q, Anil B, Tracz S, et al. (2008) Characterizing septum inhibition in *Mycobacterium tuberculosis* for novel drug discovery. *Tuberculosis* 88: 420-429.
4. Kumar K, Awasthi D, Berger W T, Tonge P J, Slayden R A, et al. (2010) Discovery of anti-TB agents that target the cell-division protein FtsZ. Future Med Chem 2: 1305-1323.
5. Slayden R A, Knudson D L, Belisle J T (2006) Identification of cell cycle regulators in *Mycobacterium tuberculosis* by inhibition of septum formation and global transcriptional analysis. Microbiology 152: 1789-1797.
6. Mathew B, Ross L, Reynolds R C (2013) A novel quinoline derivative that inhibits mycobacterial FtsZ. *Tuberculosis* 93: 398-400.
7. Mathew B, Srivastava S, Ross L J, Suling W J, White E L, et al. (2011) Novel pyridopyrazine and pyrimidothiazine derivatives as FtsZ inhibitors. Bioorg Med Chem 19: 7120-7128.
8. Huang Q, Kirikae F, Kirikae T, Pepe A, Amin A, et al. (2006) Targeting FtsZ for anti*tuberculosis* drug discovery: noncytotoxic taxanes as novel anti*tuberculosis* agents. J Med Chem 49: 463-466.
9. Huang Q, Tonge P J, Slayden R A, Kirikae T, Ojima I (2007) FtsZ: a novel target for *tuberculosis* drug discovery. Curr Top Med Chem 7: 527-543.
10. Kumar K, Awasthi D, Lee S-Y, Zanardi I, Ruzsicska B, et al. (2011) Novel trisubstituted benzimidazoles, targeting Mtb FtsZ, as a new class of antitubercular agents. J Med Chem 54: 374-381.
11. Awasthi D, Kumar K, Knudson S E, Slayden R A, Ojima I (2013) SAR Studies on Trisubstituted Benzimidazoles as Inhibitors of Mtb FtsZ for the Development of Novel Antitubercular Agents J Med Chem 56: 9756-9770.
12. Kumar K, Awasthi D, Lee S,-Y., Cummings J E, Knudson S E, et al. (2013) Benzimidazole-based antibacterial agents against *Francisella tularensis*. Bioorg Med Chem 21: 3318-3326.
13. Camus J C, Pryor M J, Medigue C, Cole S T (2002) Re-annotation of the genome sequence of *Mycobacterium tuberculosis* H37Rv. Microbiology 148: 2967-2973.
14. Lenaerts A J, Gruppo V, Brooks J V, Orme I M (2003) Rapid in vivo screening of experimental drugs for *tuberculosis* using gamma interferon gene-disrupted mice. Antimicrob Agents Chemother 47: 783-785.
15. Miyoshi-Akiyama T, Matsumura K, Iwai H, Funatogawa K, Kirikae T (2012) Complete annotated genome sequence of *Mycobacterium tuberculosis* Erdman. J Bacteriol 194: 2770.
16. Boyne M E, Sullivan T J, amEnde C W, Lu H, Gruppo V, et al. (2007) Targeting fatty acid biosynthesis for the development of novel chemotherapeutics against *Mycobacterium tuberculosis*: evaluation of A-ring-modified diphenyl ethers as high-affinity InhA inhibitors. Antimicrob Agents Chemother 51: 3562-3567.
17. Slayden R A, Lee R E, Barry C E, 3rd (2000) Isoniazid affects multiple components of the type II fatty acid synthase system of *Mycobacterium tuberculosis*. Mol Microbiol 38: 514-525.
18. Collins L, Franzblau S G (1997) Microplate Alamar blue assay versus BACTEC 460 system for high-throughput screening of compounds against *Mycobacterium tuberculosis* and *Mycobacterium avium*. Antimicrob Agents Chemother 41: 1004-1009.
19. Reddy V M, Einck L, Andries K, Nacy C A (2010) In vitro interactions between new antitubercular drug candidates SQ109 and TMC207. Antimicrob Agents Chemother 54: 2840-2846.

Example 3. Identification of Next-Generation Benzimidazole-Based Cell Division Inhibitors with Efficacy Equivalent to Isoniazid Compounds in the 2,5,6- and 2,5,7-tribstituted benzimidazoles have demonstrated antitubercular activity and efficacy in animal models of infection. We therefore performed additional studies to identify next-generation benzimidazole-based cell division inhibitors with efficacy equivalent to isoniazid.

Although there are drugs for the treatment of TB, the increasing number of clinical strains resistant to one or more of the frontline drugs in resulting in increased complications in disease management. Structure-activity relationship (SAR) and plasma/metabolic stability studies have led to the development of next-generation benzimidazoles. The lead benzimidazole compounds where evaluated for potency against *M. tuberculosis* H37Rv and representative clinical strains, toxicity and kill characteristics. Plasma and liver microsome lability studies were performed to assess compound stability. Each lead compound was delivered by intrapcritoncal (ip) and oral (po) routes to assess efficacy in the acute murine model of *tuberculosis.*

SB-P17G-A33, SB-P17G-A38 and SB-P17G-A42 exhibited minimal inhibitory concentrations of 0.16-0.47 μg/mL against *M. tuberculosis* H37Rv and representative clinical strains. SB-P17G-A33 delivered at 50 mg/kg b.i.d. via cither IP or PO reduced the bacterial load by greater than 1.7 $Log_{10}$ CFU in the lungs and greater than 2.5 $Log_{10}$ CFU in the spleen. SB-P17G-A38 and SB-P17G-A42 demonstrated much better efficacy in reducing the bacterial load by 5.5-6.3 $Log_{10}$ CFU in the lungs and 3.9-5 $Log_{10}$ CFU in the spleen.

Structure-activity relationship (SAR) and plasma/metabolic stability studies have thus led to the development of next-generation benzimidazoles with high potency and efficacy against *M. tuberculosis*. This example describes these next-generation benzimidazole-based cell division inhibitors and the evaluation thereof, showing a similar level of efficacy to isoniazid in a murine model of *M. tuberculosis* infection.

Introduction.

Globally, *tuberculosis* (TB) is the leading cause of death from a bacterial infection and latent infections provide an ongoing source of transmission, which hinders disease management efforts[1,2]. Current treatment regimens require a lengthy course of at least two front line drugs, with the addition of secondary drugs depending on drug resistance. Until bedaquiline (TMC207), which was approved in 2012 by the FDA for use against MDR strains, no new chemotherapeutics to treat *M. tuberculosis* have been added to the treatment options in forty years[3-5]. Accordingly, bedaquiline, which inhibits mycobacterial ATP synthase, is an example of how additional drugs with novel modes of action can be used effectively to augment current regimens and combat the increasing burden of multi-drug resistant clinical TB strains (MDR-, XDR-TB, TDR-TB).

In this context, the filamentous temperature sensitive protein Z (FtsZ), an essential bacterial cytokinesis protein, is a highly promising therapeutic target since the disruption of cell division results in decreased bacterial growth and ultimately viability[6,7]. FtsZ is a highly conserved and ubiquitous bacterial cell division protein. FtsZ polymerizes to form a highly dynamic cytokinetic structure, designated as the Z-ring, in the mid-cell in a GTP-dependent manner[8,9]. Upon polymerization of FtsZ, constriction of the Z-ring takes place by recruiting cell division proteins, which results in complete septum formation.

Although tubulin and FtsZ share homology and tubulin inhibitors are known to inhibit FtsZ polymerization/depolymerization balance[6,10,11], the structural diversity affords the opportunity to develop FtsZ-specific compounds with limited cytotoxicity to eukaryotic cells[12]. A number of known tubulin inhibitors were screened against Mtb by researchers at the Southern Research Institute and several pyridopyrazine- and pteridine-based FtsZ inhibitors with anti-TB activity were identified[13-15]. Also, we found that other known tubulin inhibitors, thiabendazole and albendazole, interfered and delayed the Mtb cell division processes[11]. Taking into account the structural similarity of the pyridopyrazine, pteridine, albendazole and thiabendazole skeletons[13-15], we envisioned that the benzimidazole scaffold would be a promising starting point for the development of novel FtsZ inhibitors, which will have activity against both drug sensitive and drug resistant Mtb. Because a thorough literature search found very few trisubstituted benzimidazoles and these compounds were not investigated for their antibacterial activity, 2,5,6- and 2,5,7-trisubstituted benzimidazoles, were selected as the basic scaffold for the synthesis of novel benzimidazole libraries using systematic and rational design[16].

Accordingly, libraries of 2,5,6- and 2,5,7-trisubstituted benzimidazoles were prepared and their activity against Mtb H37Rv was tested and compounds were identified with minimal inhibitory concentrations (MICs) less than 5 μg/mL. Upon further evaluation the most potent early lead compounds from the 2,5,6-trisubstituted series of benzimidazoles, SB-P3G2 and SB-P8B2 (FIG. 11), were found to exhibit excellent MIC values in the range of 0.39-1.56 μg/mL against drug resistant strains as well as a drug sensitive (H37Rv) strain[16]. Importantly, the lead compound SB-P3G2 exhibited efficacy in vivo in the acute TB infection models[17].

Because compounds in this structural class have demonstrated antitubercular activity and efficacy in animal models of infection, we performed additional SAR studies and optimized potency through systematic structural modifications at the 5 and 6 positions. These efforts led to the development of a series of highly potent lead compounds including SB-P17G-C2 with an MIC 0.06 μg/mL (FIG. 11)[18]. This series of compounds with improved potency had a 2-cyclohexyl group at C2, a carbamate group at C5 and a dialkylamino group at C6, and a dimethylamino group at C6 was found to boost the potency[18]. However, plasma and metabolic stability assessment of these lead compounds revealed that the carbamate groups at C5 are labile in plasma as well as metabolized by microsomes in mice and rats, although the stability was much higher in humans it was still considered a liability.

As a result, our efforts focused on finding highly potent compounds with an amide group, instead of a carbamate group at C5. This line of SAR study identified, SB-P17G-A20, a compound, bearing a 4-trifluoromethoxybenzoylamino group at C5[19] (FIG. 11), with MIC 0.16 μg/m. SB-P17G-A20 had excellent plasma stability (4 hours) in humans (99.9%), good stability in mice (75.6%) and moderate metabolic stability (liver microsomes) in humans (61%) and mice (55%). SB-P17G-A20 demonstrated efficacy in the acute TB model of infection as demonstrated by a reduction in the bacterial burden in the lungs and spleen by 1.73±0.24 $Log_{10}$ CFU and 2.68±$Log_{10}$ CFU, respectively[19]. Building upon the successful identification of the second-generation lead compound, SB-P17G-A20, exhibiting promising in vivo efficacy, we have continued the optimization of this series of 2,5,6-trisubstituted benzimidazoles. When we introduced a fluorine into the ortho position of the 4-trifluoromethoxybenzoyl or 4-trifluoromethylbenzoyl moiety, the plasma and metabolic stability of those analogs were found to be substantially improved, i.e., plasma stability (4 hours): 98.3-99.4% in humans and 88.5-89.3% in mice; metabolic stability (liver microsomes): 87-95% in humans and 83-96% in mice. The favorable stability profiles were reflected in the markedly enhanced in vivo efficacy of these compounds.

We report here the in vitro potency, stability and in vivo efficacy profiles of three next-generation lead compounds, SB-P17G-A33, SB-P17G-A38 and SB-P17G-A42 that were developed through SAR optimization and identified using the new in vitro-in vivo relationship selection criteria[17] (FIG. 11). All three compounds are equally potent in vitro against clinical isolates of *M. tuberculosis* with varied drug susceptibility profiles and *M. tuberculosis* H37Rv. Two of the compounds SB-P17G-A38 and SB-P17G-A42, had efficacy comparable to isoniazid in the acute murine model of *M. tuberculosis* infection. Importantly, these studies substantiate that inhibition of FtsZ and cell division with the next-generation benzimidazoles can equal the activity of a front line drug in the acute murine model of *tuberculosis* infection.

Methods.

*Mycobacterium tuberculosis* Strains, Media and Drug Conditions.

The laboratory reference strain *M. tuberculosis* H37Rv and clinical isolates, TN587, W210, NHN382 and NHN20, were used for standard MICs[11,20,21]. *M. tuberculosis* Erdman (TMCC 107) was used in the acute animal model of *M. tuberculosis* infection. For in vitro assays, *M. tuberculosis* was grown in Difco™ 7H9 Middlebrook liquid media (BD Biosciences, 271310) with 10% Middlebrook OADC Enrichment (VWR, 9000-614), 0.05% Tween (G-Biosciences, 786-519), and 0.2% Glycerol at 37° C. or *M. tuberculosis* was grown on Difco™ Middlebrook 7H11 agar (BD Biosciences, 283810) supplemented with 10% OADC. For CFU assays from animal studies the agar plates were supplemented with asparagine and antibiotics[17,19].

Isoniazid (INH) was obtained from Sigma (cat # I-3377). All compounds including, SB-P17G-A33, SB-P17G-A38 and SB-P17G-A42, used in in vitro assays were dissolved in DMSO. For the animal studies, isoniazid was dissolved in deionized water, filter sterilized, and then delivered IP q.d. The 3 benzimidazoles were dissolved in a 25% Solutol, 25% ethanol and PBS diluent and delivered IP b.i.d. to the animals. IP controls were injected with vehicle alone b.i.d. For PO delivery, isoniazid was dissolved in PBS, filter sterilized and then delivered qd. The benzimidazoles were solubilized and delivered using in house formulations consisting of 40% captex 200, 40% Solutol 15 and 20% capmul·mcm diluted with sterile deionized water prior to delivery PO b.i.d. PO controls were given the vehicle alone b.i.d.

Determination of Minimal Inhibitory Concentrations and Low Oxygen Studies.

MIC values for the lead benzimidazoles, SB-P17G-A33, SB-P17G-A38 and SB-P17G-A42, against *M. tuberculosis* and clinical isolates were determined using a modified 96-well microplate Alamar Blue assay (MABA)[16,22]. Growth inhibition response curves were generated from 4 different MABA experiments for the benzimidazoles by graphing the $Log_{10}$ drug concentrations against the difference in growth between the treated bacteria and control bacteria as described previously[17,19].

Cytotoxicity Assay.

The cytotoxicity assay was performed as described previously[16]. Briefly compounds were serially diluted in 96 well plates. Vero Cells in media with resazurin were added to each well, the plates were incubated for 72 h at 37° C., the plates were read and the $IC_{50}$ was calculated using standard procedures.

Plasma Stability Studies in Human and Mouse Plasma.

As described previously[19], blood used in the assay was collected using lithium heparin as anticoagulant. Plasma spiked with the compound was analyzed by LC-MS/MS following protein precipitation. The limit of quantification for compounds was 10 ng/mL. Chromatographic conditions for LC were as described previously. The mean percent of difference between $C_{1h}$ or $C_{4h}$ and $C_0$ concentrations were calculated using the formula; M % D (%)=100×[($C_{1h}$ or $C_{4h}$)−$C_0$]/$C_0$. The compounds were considered as stable if the mean percent of difference between $C_{4h}$ and $C_0$ concentrations was less than 20%.

Evaluation of Oxidative Metabolic Lability in Mouse/Human Liver Microsomes.

As described previously[19], microsomal fractions were prepared and SB-P17G-A33, SB-P17G-A38 or SB-P17G-A42 at 5 µM concentration were incubated with microsomal proteins (human or mouse, 1 mg/mL). The reactions were prepared as described and were run in the presence of bovine scrum albumin (BSA, 0.1%) for the duration of 0 and 20 min (with or without microsomal proteins and/or cofactors). Enzyme activity was stopped, the protein was precipitated and removed by centrifugation. The supernatant fluids were analyzed by LC/MS-MS. LC analysis for SB-P17G-A33 and SB-P17G-A42 was performed on each sample using a Hypersil Gold Thermo C18 (50 mm×2.1 mm, 1.9 µm) column. Chromatography was achieved with a 10-100% gradient of Solvent A (ammonium acetate (0.08 g)/formic acid (2 mL)/HPLC water up to 1000 mL) and Solvent B (ammonium acetate (0.08 g)/formic acid (2 mL)/methanol (200 mL)/acetonitrile up to 1000 mL) at a flow rate of 0.5 mL/min. Retention time for both SB-P17G-A33 and SB-P17G-A42 was 1.53 min. LC analysis for SB-P17G-A38 utilized a Kinetex C18 (30 mm×2.1 mm, 1.7 µm, 100 Å) column and chromatography was achieved with a 5-95% gradient of Solvent A (HPLC-grade water up to 1000 mL, 0.1% formic acid) and Solvent B (acetonitrile up to 1000 mL, 0.1% formic acid) at a flow rate of 0.75 mL/min, t=0-1.5 min. Retention time for SB-P17G-A38 was 0.68 min. A Thermo Finnigan TSQ Quantum Ultra instrument, ESI positive ion ionization mode was used for MS/MS. Each compound was studied in duplicates. Results are expressed in percentage of lability (or total metabolism) using the following formula: Total metabolism=[1−(UC_Peak Area+Cofactor at T20)/(UC_Peak Area Reference at T0)]×100 where UC=Unchanged Compound; "Reference" sample was NADPH for liver microsomal preparation.

Acute Murine Model of *Tuberculosis*.

The acute mouse model used to assess efficacy of lead compounds has been described previously[17,19]. Briefly, *M. tuberculosis* strain Erdman was delivered via low dose aerosol to C57BL/6-Ifngtm1ts (Jackson Laboratories, Bar Harbor, Me.). Drugs were delivered 50 mg/kg b.i.d. IP or PO days 5-14 post-infection. Isoniazid was delivered 25 mg/kg q.d. IP and PO controls were infected and treated with vehicle only b.i.d. Animals were sacrificed on day 15 post-infection, the organs were homogenized in saline, diluted, and plated. In addition to the serial dilutions, the rest of the homogenized organs were plated for Isoniazid and the benzimidazole treated animals. Bacterial colonies were counted, the colony counts were converted to logarithms and outliers were identified by the Grubbs' Test. One-way t-tests (95% confidence interval). One-way ANOVA and Tukey's Multiple Comparison Test were performed for statistical analysis.

Results.

Next-Generation Lead Compounds have Enhanced In Vitro Potency Against *M. tuberculosis*.

Previously we reported that a series of 2,5,6- and 2,5,7-trisubstituted benzimidazoles demonstrated activity against *M. tuberculosis* H37Rv and representative clinical isolates with different susceptibilities to therapeutic *tuberculosis* drugs (FIG. 1)[16,18,19,21]. While these compounds demonstrated potency, their efficacy was modest, attributed to their low-modest plasma/metabolic stability. Accordingly, through optimization based on SAR and plasma/metabolic stability studies, newer analogs were designed and synthesized, which led to the next generation of compounds (FIG. 11). These, next-generation, lead compounds SB-P17G-A33, SB-P17G-A38 and SB-P17G-A42 demonstrated enhanced potency against *M. tuberculosis* H37Rv as evident from MICs of 0.39±0.16 µg/mL, 0.31±0.22 µg/mL and 0.18±0.1 µg/mL, respectively, and were not cytotoxic at 200 µg/ml in Vero cells (Table 3.1).

TABLE 3.1

Susceptibility (µg/mL) of M. tuberculosis strains and clinical isolates to SB-P17G-A33, SB-P17G-A38 and SB-P17G-A42.

| Compound | H37RV | NHN382 | TN587 | W210 | NHN20 | Vero Cells |
|---|---|---|---|---|---|---|
| SB-P17G-A33 | 0.39 ± 0.16 n = 4 | 0.37 ± 0.24 n = 3 | 0.31 ± 0 n = 2 | 0.47 ± 0.22 n = 2 | 0.39 ± 0.33 n = 2 | >200 |
| SB-P17G-A38 | 0.31 ± 0.22 n = 4 | 0.31 ± 0 n = 2 | 0.31 ± 0 n = 2 | 0.47 ± 0.22 n = 2 | 0.24 ± 0.11 n = 2 | >200 |
| SB-P17G-A42 | 0.18 ± 0.1 n = 4 | 0.16 ± 0 n = 2 | 0.24 ± 0.11 n = 2 | 0.31 ± 0 n = 2 | 0.16 ± 0 n = 2 | N/A |

Figure 12:
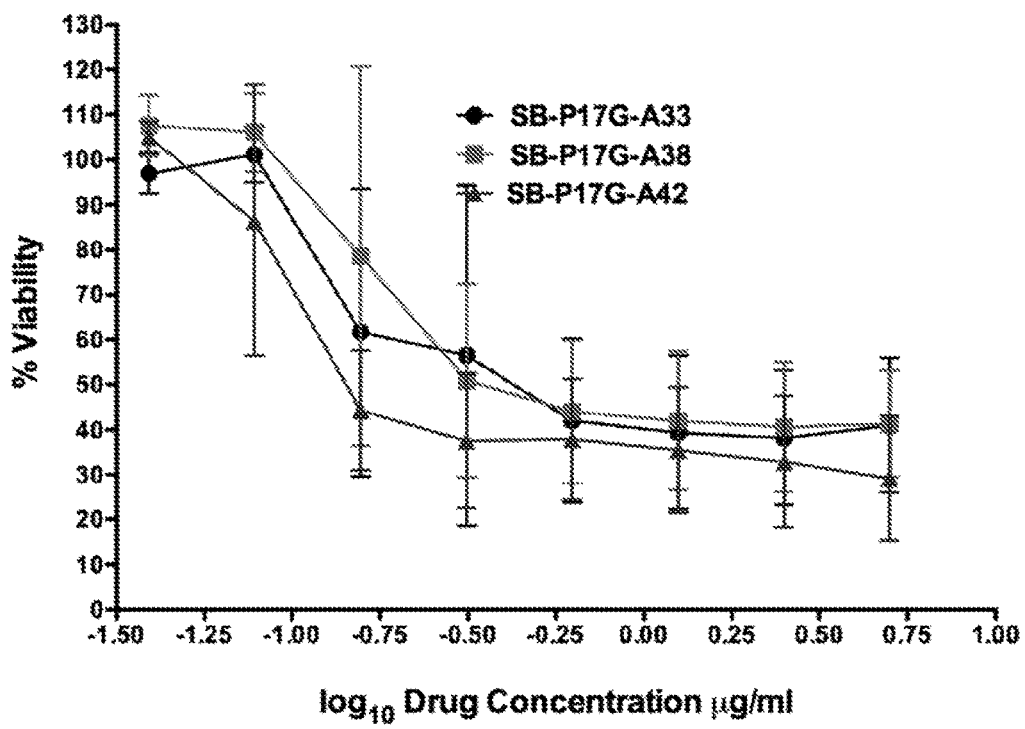
FIG. 12. In vitro activity of SB-P17G-A33, SB-P17G-A38 and SB-P17G-A42 against *M. tuberculosis*. Dose response curves were generated from MABA data for *M. tuberculosis* strains (H37Rv,) treated with the three compounds. Four different experiments were combined to generate the SD for the curves. The curves were generated by graphing the $\log_{10}$ drug concentrations against the difference in growth between the drug treated and control using GraphPad Prism Version 5.0d for Mac OS X (GraphPad Software, San Diego Calif., USA, www.graphpad.com).

These lead compounds displayed sigmoidal inhibition curves, which has been discovered to be an important characteristic of an in vitro-in vivo relationship (FIG. 12). In the past, the MIC's for the benzimidazoles tested against M. tuberculosis H37Rv and against the different clinical strains were shown to be equally potent against drug-sensitive and drug-resistant strains of M. tuberculosis[16,18,19]. Consistent with previous results, all three of the next-generation compounds were equally potent against M. tuberculosis H37Rv and the representative clinical strains examined.

Figure 13:
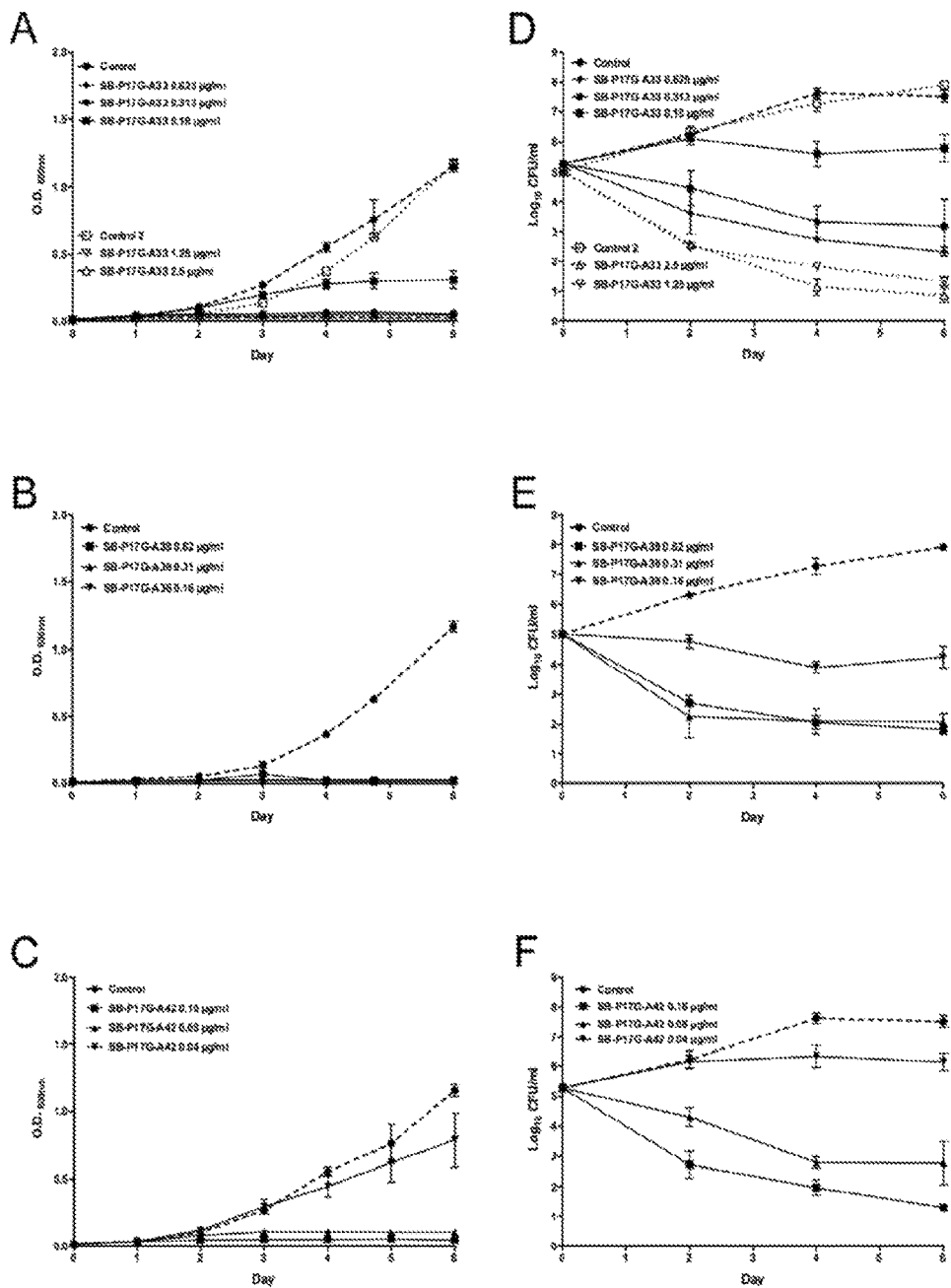
FIG. 13. Killing characteristics of SB-P17G-A33, SB-P17G-A38 and SB-P17G-A42 against whole bacteria. Separate curves were generated for each compound. The time dose curves were generated from $OD_{600\ nm}$ (A-C) and from CFU enumeration (D-F) data. Different concentrations of the compound were tested in triplicate and the mean and standard deviation of the $OD_{600\ nm}$ values or the CFU counts from Day 0, 2, 4, and 6 were plotted against time using GraphPad Prism Version 5.0d for Mac OS X (GraphPad Software, San Diego Calif., USA, www.graphpad.com).
Figure 14:
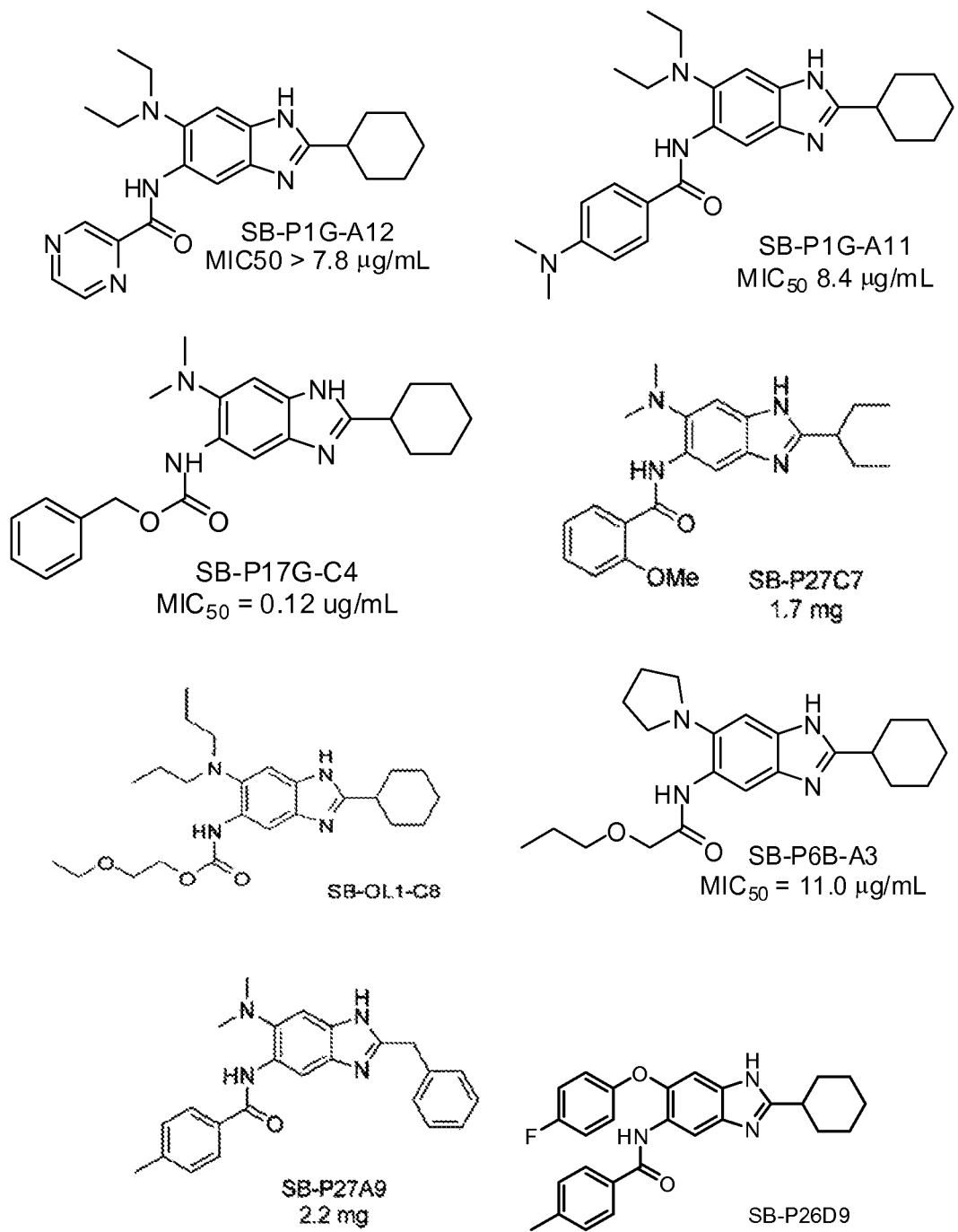
FIG. 14. Chemical structures of certain 2,5,6-trisubstituted benzimidazoles.
Figure 14:
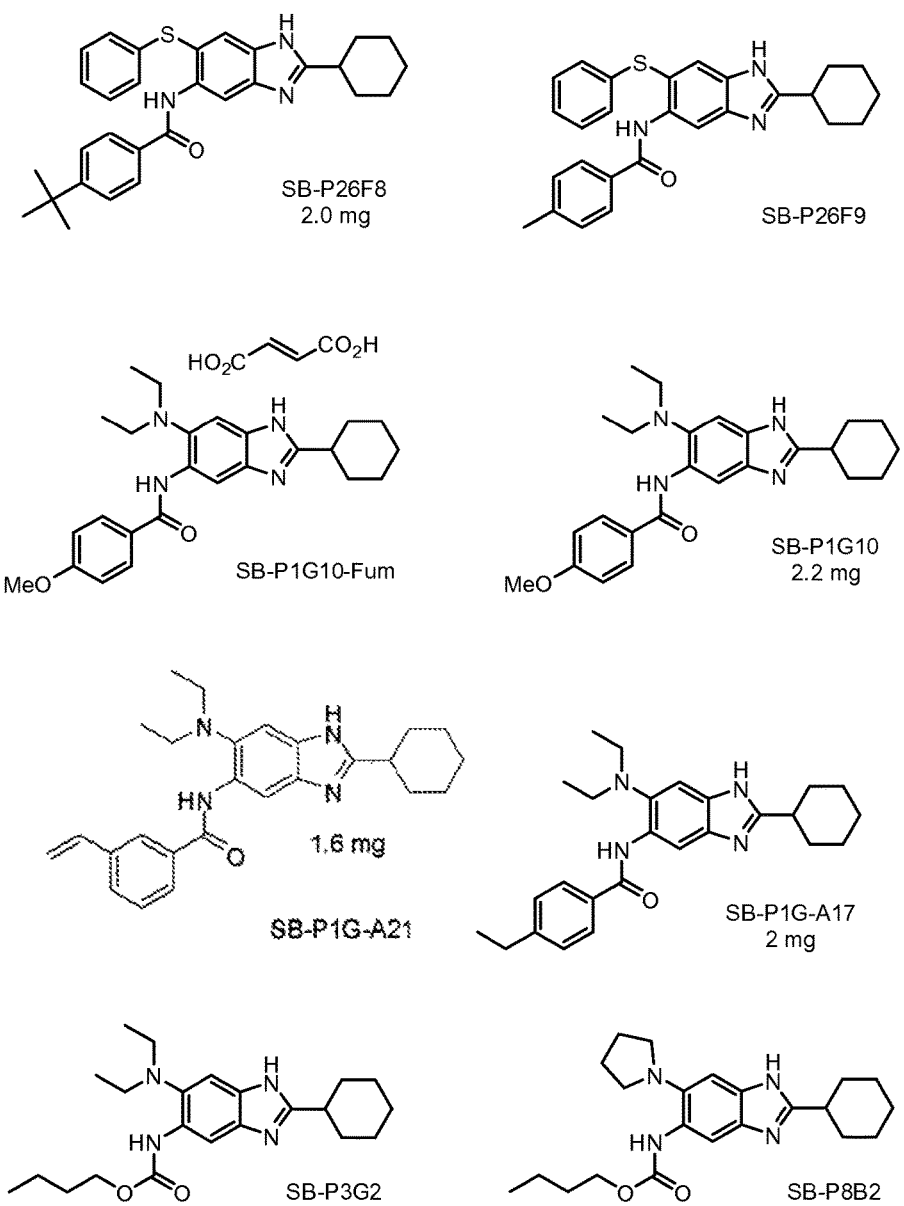
Figure 14:
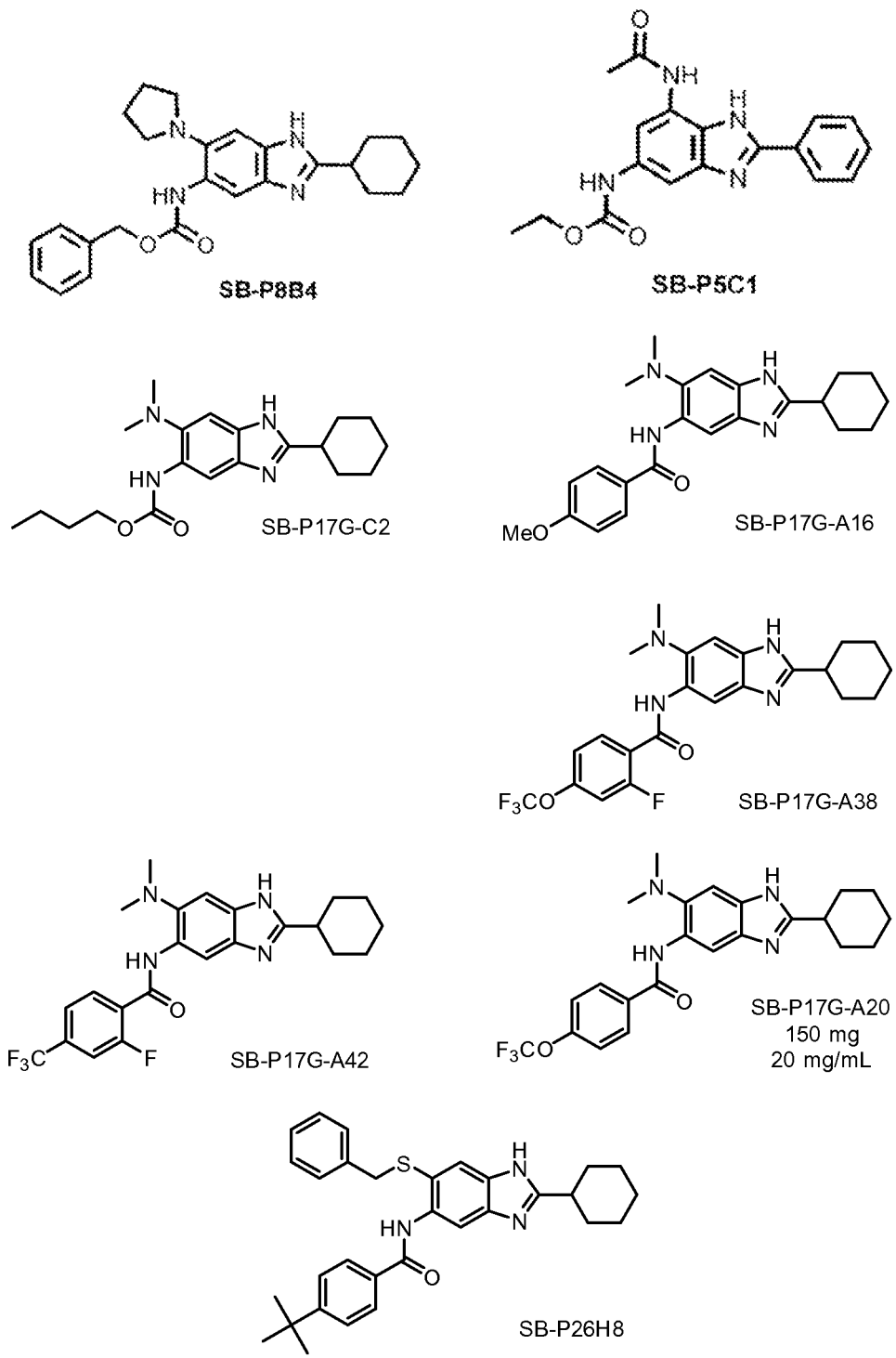

To investigate the kill characteristics of the compounds against M. tuberculosis, time dose curves were generated (FIG. 13 A-F). The growth curve of M. tuberculosis in the presence of each of the compounds at different concentrations showed that all three compounds are concentration dependent inhibitors. SB-P17G-A38 reduced the number of bacteria by 2.8 $Log_{10}$ CFU at 1×MIC by day 2 and by 2.9 $Log_{10}$ CFU at day 6 (FIG. 13A-C). SB-P17G-A42 reduced the number of viable bacteria by 2.5 $Log_{10}$ CFU at day 2 at 1×MIC and continued to reduce the number of viable bacteria through day 6 by almost 4 $Log_{10}$ CFU (FIG. 13F). SB-P17G-A33 demonstrated less bactericidal activity reducing the bacterial load only 0.8-1.7 $Log_{10}$ CFU during the First 2 days when dosed at MIC levels (FIG. 13D). In addition. SB-P17G-A38 required 3-6×MIC to reduce the bacterial viability by 3.6-4.4 $Log_{10}$ CFU, which is an equivalent level of reduction as to 1× of the other two lead compounds (FIG. 13E).

Plasma Stability and Metabolic Liability of SB-P17G-A33, SB-P17G-A38 and SB-P17G-A42.

Compounds with poor plasma stability often have short $t_{1/2}$ and high clearance. To assess the potential in vivo pharmacokinetics (PIC), the stability of SB-P17G-A33 and SB-P17G-A38 were evaluated in the presence of human and mouse plasma. SB-P17G-A33 and SB-P17G-A38 were found to be stable in human plasma with only 1% and 2% hydrolysis, respectively after 4 h of incubation (Table 3.2).

TABLE 3.2

Plasma stability and liver microsome lability of SB-P17G-A33, A38 and A42.

| | Plasma Stability (% hydrolysis) | | Liver Microsome Lability | |
|---|---|---|---|---|
| Compound | Human (4 h) | Mouse (4 h) | Human | Mouse |
| SB-P17G-A33 | −0.6 | −10.7 | 5% | 17% |
| SB-P17G-A38 | −1.7 | −11.5 | 13% | 4% |
| SB-P17G-A42 | ND | ND | 12% | 13% |

ND = Not Determined

Metabolic stability is also often a major limitation for lead drug candidates. To assess the extent of metabolic conversion SB-P17G-A33, SB-P17G-A38 and SB-P17G-A42 were evaluated using a microsomal stability assay. SB-P17G-A33, SB-P17G-A38 and SB-P17G-A42 exhibited only slight lability in the presence of liver microsomes with 5, 13 and 12% conversion in human liver microsomes and 17, 4 and 13% conversion in mouse liver microsomes, respectively (Table 3.2).

SB-P17G-A33, SB-P17G-A38 and SB-P17G-A42 Demonstrate Efficacy in a *Tuberculosis* Murine Model of Infection.

To evaluate efficacy, SB-P17G-A33, SB-P17G-A38 and SB-P17G-A42 were assessed in a rapid acute murine model of M. tuberculosis infection (Table 3.3). Each compound was delivered 50 mg/kg IP and PO b.i.d. beginning day 5 post infection and continuing to the endpoint of day 15. SB-P17G-A38 reduced the bacterial load in the lungs by $Log_{10}$ 6.1 CFU when delivered PO and reduced the load in the lungs by $Log_{10}$ 6.3 CFU when delivered IP.

TABLE 3.3

In vivo efficacy of SB-P17G-A33, SB-P17G-A38 and SB-P17G-A42 in the murine model of M. tuberculosis infection when delivered IP or PO b.i.d. Difference in $Log_{10}$ CFU between the means from the Test and Control Groups

| | Route | $Log_{10}$CFU Lungs | Δ | $Log_{10}$CFU Spleen | Δ |
|---|---|---|---|---|---|
| Control | IP | 6.69 ± 0.05 n = 2 | N/A | 4.96 ± 0.43 n = 2 | N/A |
| | PO | 6.31 ± 0.04 n = 5 | N/A | 3.89 ± 0.56 n = 5 | N/A |
| SB-P17G-A33 | IP | 4.59 ± 0.71 n = 3 | −2.10** | 1.60 ± .0 n = 3 | −3.36*** |
| | PO | 4.58 ± 0.21 n = 5 | −1.72*** | 1.40 ± 1.24 n = 5 | −2.49*** |
| SB-P17G-A38 | IP | 0.39 ± 0.63 n = 4 | −6.30*** | 0 ± 0 n = 4 | −4.96*** |
| | PO | 0.22 ± 0.34 n = 5 | −6.10*** | 0 ± 0 n = 5 | −3.89*** |
| SB-P17G-A42 | IP | 0.91 ± 0.64 n = 4 | −5.78*** | 0 ± 0 n = 4 | −4.96*** |
| | PO | 0.66 ± 0.43 n = 5 | −5.65*** | 0 ± 0 n = 5 | −3.89*** |

TABLE 3.3-continued

In vivo efficacy of SB-P17G-A33, SB-P17G-A38 and SB-P17G-A42 in the murine model of M. tuberculosis infection when delivered IP or PO b.i.d.
Difference in $Log_{10}$ CFU between the means from the Test and Control Groups

|     | Route | $Log_{10}$CFU Lungs | | | Δ | $Log_{10}$CFU Spleen | | | Δ |
|-----|-------|---------|---|---|---|---------|---|---|---|
| Inh | IP | 0.12 ± 0.16 | n = 5 | | −6.57*** | 0 ± 0 | n = 5 | | −4.96*** |
|     | PO | 0 ± 0 | n = 5 | | −6.31* | 0 ± 0 | n = 5 | | −3.89* | n = number of animals survived;
 <.01, * <.001 significance from Tukey Test.

In one of the 5 animals treated with SB-P17G-A38 PO the lungs appeared cleared of bacteria and one of the 4 animals treated with SB-P17G-A38 IP the lungs appeared clear. Similarly, SB-P17G-A42 reduced the bacterial load in the lungs by 5.6 $Log_{10}$ CFU when delivered PO and reduced the load in the lungs by 5.8 $Log_{10}$ CFU when delivered IP. In one of the 5 animals treated with SB-P17G-A42 PO, the lungs appeared cleared of bacteria and all of the animals treated with SB-P17G-A42 IP had some counts in the lungs. Importantly, SB-P17G-A38 and SB-P17G-A42 demonstrated efficacy comparative to the front-line and gold standard Mtb drug isoniazid, which was delivered IP 20 mg/kg q.d. as a positive control. Further, there were no detectable bacteria in the spleen in the SB-P17G-A38 and SB-P17G-A42 treated groups when delivered either IP or PO. Although treatment with SB-P17G-A33 resulted in a statistically significant 1.7 and 2.5 $Log_{10}$ CFU reduction in bacterial load in the lungs and spleen, the observed efficacy with SB-P17G-A33 treatment was modest in comparison to SB-P17G-A38 and SB-P17G-A42 and isoniazid.

To assess the potential for the development of drug resistance, spontaneous resistance from mono-drug therapy was assessed by plating bacteria isolated from mouse tissue on plates containing different concentrations of the respective drug and compound free medium. No colonies grew on medium containing greater than 1.6 μg/mL of drug, therefore demonstrating that no drug resistance developed during the drug treatment in the animals.

Discussion.

*Tuberculosis* is one of the leading causes of death and the emergence of *M. tuberculosis* strains that are resistant to frontline TB drugs has hindered the management and control of this disease. As a part of our drug discovery program we have been focusing on 2,5,6- and 2,5,7-trisubstituted benzimidazoles for the development of new chemotherapeutics against *M. tuberculosis*. Initially, we identified several lead 2,5,6-trisubstituted benzimidazoles, such as SB-P3G2 and SB-P8B2, which demonstrated the same level of antibacterial activity against *M. tuberculosis* and clinical isolates, including drug resistant strains[16,17]. SB-P3G2 was shown to inhibit FtsZ polymerization in a dose dependent manner and increase the GTPase activity that promotes FtsZ polymerization and the formation of FtsZ polymers[16].

The optimization of early lead compounds in this structural class was performed on the objective to improve potency against whole bacteria based on antibacterial activity assays against Mtb H37Rv and mitigation of toxicity in standard toxicity assays. As progress was being made, the emphasis included efficacy in the animal model of infection. Along the way, it was discovered that additional in vitro-in vivo relationship criteria could be used to identify leads with efficacy in animal models. Concomitant, lead compounds where assessed for metabolic liabilities. This process led to the identification of a highly potent lead compound SB-P17G-C2 (MIC 0.06 μg/mL), bearing a 2-cyclohexyl group at C2, a carbamate group at C5 and a dimethylamino group at C6, as well as other congeners[18]. The introduction of a dimethylamino group at C6 was found to boost the potency. However, the examination of the plasma and metabolic stability revealed that the carbamate groups at C5 are labile in plasma susceptible to metabolism by microsomes. This finding was consistent with the observed lack of significant efficacy. Accordingly, efforts focused on reducing the metabolic liability of the carbamate, which resulted in finding that compounds with an amide group at C5, in place of a carbamate group, had comparable potency against whole bacteria. Ultimately, this line of investigation led to the discovery of SB-P17G-A20 (MIC 0.16 μg/mL), bearing a 4-trifluoromethoxy-benzoylamino group at C5, with good plasma stability and moderate metabolic stability in mice. SB-P17G-A20 exhibited promising efficacy in the acute TB infection model in GKO mice: bacterial load reduction in the lungs and spleen by 1.73 and 2.68 $Log_{10}$ CFU, respectively[19].

The optimization process of the SB-P17G-A20 series of benzimidazoles was continued and it was discovered that the introduction of a fluorine into the ortho position of the 4-trifluoromethoxybenzoyl or 4-trifluoromethylbenzoyl moiety substantially improved the plasma and metabolic stability. Indeed, the in vivo efficacy of these next-generation lead compounds, SB-P17G-A33, SB-P17G-A38 and SB-P17G-A42, was markedly enhanced, due to their favorable PK profiles as compared to that of SB-P17G-A20. In vivo efficacy study was performed at 50 mg/kg IP and PO b.i.d., beginning day 5 post infection and continuing to the endpoint of day 15. SB-P17G-A38 and SB-P17G-A42 reduced the bacterial load in the lungs by 6.1-6.3 and 5.6-5.8 $Log_{10}$ CFU, respectively. SB-P17G-A33 showed lower efficacy (bacterial load reduction in lungs by 1.72-2.10 $Log_{10}$ CFU). Moreover, no detectable bacteria were present in the spleen in the SB-P17G-A38 and SB-P17G-A42 treated groups (both IP and PO). It is worthy of note that SB-P17G-A38 and SB-P17G-A42 demonstrated efficacy comparative to the front-line and gold standard Mtb drug isoniazid, which was used as a control.

In our continued interest in the development of novel antimycobacterial chemotherapeutics, we have developed and optimized a third series of substituted benzimidazoles based on our evaluations described herein. The lead compounds from this series has greatly improved efficacy in the animal model of *M. tuberculosis* infection. Notably, the efficacy of SB-P17G-A38 and SB-P17G-A42 in the acute animal model of infection is comparable to the efficacy of isoniazid. No trisubstituted-benzimidazole-resistant mutants have been detected in vitro or in vivo studies thus far, which is consistent with our previous observations that indicate interfering with proper FtsZ polymerization and septum formation results in inhibition and lethality[23,24]. The improved efficacy of the trisubstituted benzimidazoles in the acute murine model and the lack of resistance mutants shows that this class of compounds can be a chemotherapeutic against *tuberculosis*.

CITATIONS

1. Raviglione, M. C. & Smith, I. M. XDR *tuberculosis*—implications for global public health. *The New England journal of medicine* 356, 656-659 (2007).
2. Migliori, G. B., De Iaco, G., Besozzi, G., Centis, R. & Cirillo, D. M. First *tuberculosis* cases in Italy resistant to all tested drugs. *Euro surveillance: bulletin europeen sur les maladies transmissibles=European communicable disease bulletin* 12, E070517 070511 (2007).
3. Andries, K., et al. A diarylquinoline drug active on the ATP synthase of *Mycobacterium tuberculosis*. *Science* 307, 223-227 (2005).
4. Diacon, A. H., et al. The diarylquinoline TMC207 for multidrug-resistant *tuberculosis*. *The New England journal of medicine* 360, 2397-2405 (2009).
5. Matteelli, A., Carvalho, A. C., Dooley, K. E. & Kritski. A. TMC207: the first compound of a new class of potent anti-*tuberculosis* drugs. *Future Microbiol* 5, 849-858 (2010).
6. Vollmer, W. The prokaryotic cytoskeleton: A putative target for inhibitors and antibiotics?*Appl. Microbiol. Biotechnol.* 73, 37-47 (2006).
7. Margalit. D. N., et al. Targeting cell division: small-molecule inhibitors of FtsZ GTPase perturb cytokinetic ring assembly and induce bacterial lethality. *Proc. Natl. Acad. Sci. U.S.A.* 101, 11821-11826 (2004).
8. Errington, J., Daniel. R. A. & Scheffers, D.-J. Cytokinesis in bacteria. *Microbiol. Mol. Biol. Rev.* 67, 52-65 (2003).
9. Bi, E. F. & Lutkenhaus, J. FtsZ ring structure associated with division in *Escherichia coli*. *Nature* 354, 161-164. (1991).
10. Huang, Q., Tonge. P. J., Slayden, R. A., Kirikae, T. & Ojima, I. FtsZ: a novel target for *tuberculosis* drug discovery. *Current Topics in Medicinal Chemistry* (Sharjah, United Arab Emirates) 7, 527-543 (2007).
11. Slayden, R. A., Knudson, D. L. & Belisle, J. T. Identification of cell cycle regulators in *Mycobacterium tuberculosis* by inhibition of septum formation and global transcriptional analysis. *Microbiology* (Reading, United Kingdom) 152, 1789-1797 (2006).
12. Nogales, E. & Wang, H. W. Structural Mechanisms Underlying Nucleotide-Dependent Self-Assembly of Tubulin and Its Relatives. *Curr. Opin. Struct. Biol.* 16, 221-229 (2006).
13. White, E. L., et al. Slow polymerization of *Mycobacterium tuberculosis* FtsZ. *J. Bacteriol.* 182, 4028-4034. (2000).
14. White, E. L., Suling, W. J., Ross, L. J., Seitz, L. E. & Reynolds, R. C. 2-Alkoxycarbonylaminopyridines: inhibitors of *Mycobacterium tuberculosis* FtsZ. *J. Antimicrob. Chemother.* 50, 111-114. (2002).
15. Reynolds, R. C., Srivastava, S., Ross. L. J., Suling. W. J. & White, E. L. A new 2-carbamoyl pteridine that inhibits mycobacterial FtsZ. *Bioorg. Med. Chem. Lett.* 14, 3161-3164 (2004).
16. Kumar, K., et al. Novel Trisubstituted Benzimidazoles, Targeting Mtb FtsZ, as a New Class of Antitubercular Agents. *J. Med. Chem.* 54, 374-381 (2011).
17. Knudson, S. E., Kumar, K., Awasthi, D., Ojima, I. & Slayden, R. A. In vitro-in vivo activity relationship of substituted benzimidazole cell division inhibitors with activity against *Mycobacterium tuberculosis*. *Tuberculosis* 94, 271-276 (2014).
18. Awasthi, D., Kumar, K., Knudson, S. E., Slayden, R. A. & Ojima, I. SAR Studies on Trisubstituted Benzimidazoles as Inhibitors of Mtb FtsZ for the Development of Novel Antitubercular Agents *Journal of medicinal chemistry* 56, 9756-9770 (2013).
19. Knudson, S. E., et al. A trisubstituted benzimidazole cell division inhibitor with efficacy against *Mycobacterium tuberculosis*. PLoS One 9, e93953 (2014).
20. Camus, J. C., Pryor, M. J., Medigue, C. & Cole, S. T. Re-annotation of the genome sequence of *Mycobacterium tuberculosis* H37Rv. *Microbiology* 148, 2967-2973 (2002).
21. Slayden. R. A., Lee. R. E. & Barry, C. E., 3rd. Isoniazid affects multiple components of the type II fatty acid synthase system of *Mycobacterium tuberculosis*. *Molecular microbiology* 38, 514-525 (2000).
22. Collins, L. & Franzblau, S. G. Microplate Alamar blue assay versus BACTEC 460 system for high-throughput screening of compounds against *Mycobacterium tuberculosis* and *Mycobacterium avium*. *Antimicrobial agents anti chemotherapy* 41, 1004-1009 (1997).
23. Respicio, L., et al. Characterizing septum inhibition in *Mycobacterium tuberculosis* for novel drug discovery. *Tuberculosis* 88, 420-429 (2008).
24. Slayden, R. A., Knudson. D. L. & Belisle, J. T. Identification of cell cycle regulators in *Mycobacterium tuberculosis* by inhibition of septum formation and global transcriptional analysis. *Microbiology* 152, 1789-1797 (2006).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for detecting bactericidal antibacterial compounds, the method comprising:
    (a) measuring the minimal inhibitory concentration (MIC) in vitro of a pool of antibacterial compounds with respect to an infectious bacteria selected from the group consisting of replicating or non-replicating bacilli and *M. tuberculosis;*
    (b) selecting one or more compounds from the pool of compounds, wherein the one or more selected compounds have a lower MIC than the MIC of 50% of the pool of compounds;
    (c) measuring the drug concentration response curve (kill-curve) of the selected compounds with respect to the infectious bacteria;
    (d) identifying compounds from step (c) that display a zonal kill-curve, which zonal kill-curve is characterized by a narrow range of concentrations of effective bactericidal activity wherein the narrow range is about 0.5×MIC to about 4×MIC, thereby indicating bacteriostatic activity above the MIC;

(e) identifying compounds from step (c) that display a sigmoidal kill-curve, which sigmoidal kill-curve is characterized by an inhibitory threshold as the concentration of the compound increases, thereby indicating bactericidal activity at the inhibitory threshold;

f) eliminating the compounds identified in step (d) from the compounds measured in step (c); and (g) measuring the in vitro metabolic stability of one or more remaining compounds in step (f);

wherein one or more metabolically stable bactericidal compounds are detected in the pool of the one or more remaining antibacterial compounds of step (g), wherein a metabolically stable compound:

(i) has less than 2% hydrolysis rate in human plasma and less than 15% hydrolysis rate in mouse plasma, each over a four hour period; or (ii) has less than 15% conversion rate in the presence of human liver microsomes and less than 20% conversion rate in the present of mouse liver microsomes.

2. The method of claim 1 further comprising selecting one or more metabolically stable bactericidal compounds detected in step (g) for in vivo profiling in *M. tuberculosis* animal models of infection.

3. The method of claim 1 wherein one or more compounds that display a zonal kill-curve display a compound-tolerant phenotype by eliciting a stress/adaptive response when assessing the drug concentration response curve of the one or more compounds.

4. The method of claim 1 wherein the pool of compounds is evaluated for activity against clinical strains of *M. tuberculosis.*

5. The method of claim 1 wherein the pool of compounds is evaluated for activity against non-replicating bacilli.

6. The method of claim 4 wherein *M. tuberculosis* is multidrug resistant (MDR) *M. tuberculosis.*

7. The method of claim 1 wherein the one or more selected compounds having MIC lower than the MIC of 50% of the pool of compounds are identified, thereby forming a first subset of compounds, and the efficacy of the first subset of compounds is measured in an animal model of infection.

8. The method of claim 7 wherein the animal model is a murine model of *tuberculosis.*

9. The method of claim 1 wherein one or more of the compounds in the pool of compounds kill *M. tuberculosis* cells or inhibit the growth of *M. tuberculosis* cells with an $MIC_{50}$ of less than about 15 μg/mL.

10. The method of claim 1 wherein the pool of compounds comprises 2,5,6-trisubstituted benzimidazoles, 2,5,7-trisubstituted benzimidazoles, or a combination thereof.

11. The method of claim 1 wherein the pool of compounds comprises 2,5,6-trisubstituted benzimidazoles and the 2,5,6-trisubstituted benzimidazoles comprise a compound illustrated in one of FIGS. 5-6, 11, and 14, or comprises one or more of SB-P1G10, SB-P3G2, SB-P8B2, SB-P17-A38 and SB-P17-A42:

SB-P1G10

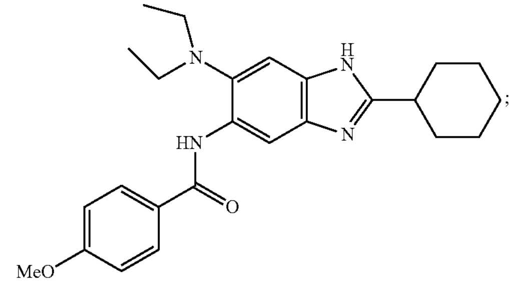

;

SB-P3G2

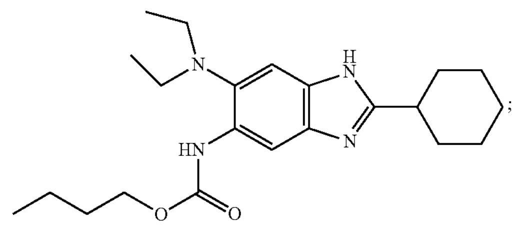

;

SB-P8B2

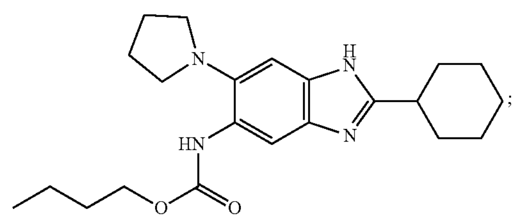

;

SB-P17G-A38

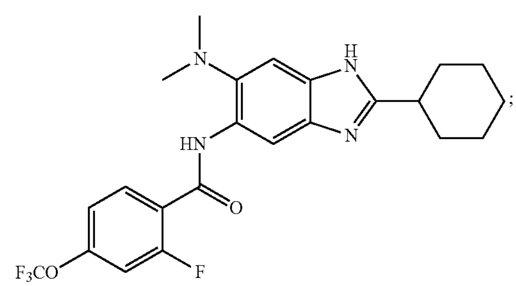

;

SB-P17G-A42

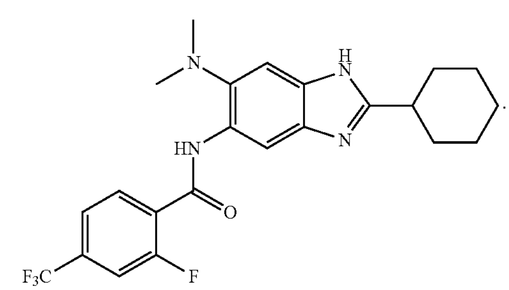

.

12. The method of claim 1 wherein the one or more selected compounds having MIC lower than the MIC of 50% of the pool of compounds are identified, forming a first subset of compounds, and one or more compounds of the first subset are evaluated in a long-term murine model of *tuberculosis.*

13. The method of claim 1 wherein the one or more selected compounds having MIC lower than the MIC of 50% of the pool of compounds are evaluated in PK/PD studies.

14. The method of claim 1 wherein the one or more of the selected compounds having MIC lower than the MIC of 50% of the pool of compounds are not antagonistic with a second antibacterial drug.

15. The method of claim 1 wherein the one or more of the selected compounds having MIC lower than the MIC of 50% of the pool of compounds are not antagonistic or are synergistic with a second antibacterial drug.

16. The method of claim 14 wherein the second antibacterial drug is isoniazid, bedaquiline, pyrazinamide, rifampin, ethambutol, or metronidazole.

\* \* \* \* \*